US008759595B2

(12) United States Patent
Peterson et al.

(10) Patent No.: US 8,759,595 B2
(45) Date of Patent: Jun. 24, 2014

(54) METHOD OF BIOBASED CHEMICAL PRODUCTION FROM CRUDE BIOGLYCERIN

(75) Inventors: John R. Peterson, Chardon, OH (US); Christopher M. Yost, Ayr (CA)

(73) Assignee: Vertichem Corporation, Cambridge, Ontario (CA)

( * ) Notice: Subject to any disclaimer, the term of this patent is extended or adjusted under 35 U.S.C. 154(b) by 127 days.

(21) Appl. No.: 13/271,925

(22) Filed: Oct. 12, 2011

(65) Prior Publication Data

US 2013/0096326 A1    Apr. 18, 2013

(51) Int. Cl.
*C07C 29/74*    (2006.01)
*C07C 29/76*    (2006.01)

(52) U.S. Cl.
USPC .......................... 568/870; 568/868; 568/869

(58) Field of Classification Search
USPC ........................................ 568/870, 868, 869
See application file for complete search history.

(56) References Cited

U.S. PATENT DOCUMENTS

| | | | |
|---|---|---|---|
| 522,132 | A | 6/1894 | Van Ruymbeke |
| 568,219 | A | 9/1896 | Ruymbeke |
| 4,100,016 | A | 7/1978 | Diebold et al. |
| 4,655,879 | A | 4/1987 | Brockmann et al. |
| 4,764,596 | A | 8/1988 | Lora et al. |
| 6,822,105 | B1 | 11/2004 | Luxem et al. |
| 7,126,032 | B1 | 10/2006 | Aiken |
| 7,667,081 | B2 | 2/2010 | Rezkallah |
| 7,718,833 | B2 | 5/2010 | Potthast et al. |
| 7,871,448 | B2 | 1/2011 | Jackam et al. |
| 7,955,402 | B2 | 6/2011 | Rabello et al. |
| 8,022,257 | B2 | 9/2011 | Li et al. |
| 8,088,183 | B2 | 1/2012 | Jackam et al. |
| 2008/0299629 | A1 | 12/2008 | Hallberg et al. |
| 2009/0117226 | A1 | 5/2009 | Hallberg et al. |
| 2009/0118477 | A1 | 5/2009 | Hallberg et al. |
| 2009/0137851 | A1 | 5/2009 | Potthast et al. |
| 2009/0198088 | A1 | 8/2009 | Tirio et al. |
| 2010/0144892 | A1 | 6/2010 | Wu et al. |
| 2011/0004031 | A1 | 1/2011 | Cruz et al. |
| 2011/0112336 | A1 | 5/2011 | Macret et al. |

FOREIGN PATENT DOCUMENTS

WO    2011030204 A1    3/2011

OTHER PUBLICATIONS

E. Kendall Pye, et al., The Alcell process, Mar. 1991 Tappi Journal.
Yonghao Ni, et al, Lignin removal from Alcell pulp by washing with ethanol and water, vol. 79: No. 3, Tappi Journal.
Waranyou Sridach, The Environmentally Benign Pulping Process of Non-Wood Fibers, Suranaree J. Sci. Technol. 17(2): 105-123.
J. Y. Zhu, et al., Pretreatment of woody biomass for biofuel production: energy efficiency, technologies, and recalcitrance, Appl Microbiol Biotechnol (2010) 87:847-857.
Annie Ng Su Nie, Characterization of Recovered Black Liquor and Isolated Lignin from Oil Palm Empty Fruit Bunch Soda Pulping for Semichemical and Chemical Pulps, Jun. 2008.
Xuejun Pan, et al., Bioconversion of Hybrid Poplar to Ethanol and Co-Products Using an Organosolv Fractionation Process: Optimization of Process Yields, Wiley Periodicals, Inc., 2006.
Esa Muurinen, Organosolv Pulping, 2000.
Maria Gonzalez Alriols, et al., Lignocellulosic biorefinery processes energy integration, Chemical Engineering Transactions, vol. 21, 553-558, 2010.
James E. Miller, et al., Batch Microreactor Studies of Lignin Depolymerization by Bases. 1 Alcohol Solvents, Sandia National Laboratories, 2002.
Virginia Marie Roberts, Homogeneous and heterogeneous catalyzed hydrolysis of lignin, 2008.
Francesco Zimbardi, et al., Technoeconomic Study on Steam Explosion Application in Biomass Processing, Applied Biochemistry and Biotechnology, vols. 98-100, 2002.
Morris Wayman, et al., Hydrolysis of Biomass by Sulphur Dioxide, Biomass 6 (1984) 183-191.
J.Y. Zhu, Sulfite pretreatment (SPORL) for robust enzymatic saccharification of spruce and red pine, Bioresource Technology 100 (2009) 2411-2418.
M. Heitz, et al., Fractionation of Populus tremuloides at the Pilot Plant Scale: Optimization of Steam Pretreatment Conditions using the STAKE II Technology, Bioresource Technology 35 (1991) 23-32.
Jiebing Li, et al., Lignin depolymerization/repolymerization and its critical role for delignification of aspen wood by steam explosion, Bioresource Technology 98 (2007) 3061-3068.
Lian-Hui Zhang, et al., Effect of steam explosion on biodegradation of lignin in wheat straw, Bioresouce Technology 98 (2008) 8512-8515.
Jiebing Li, et al., Steam explosion lignins; their extraction, structure and potential as feedstock for biodiesel and chemicals, Bioresource Technology 100 (2009) 2556-2561.
J.Y. Zhu, et al., Woody biomass pretreatment for cellulosic ethanol production: Technology and energy consumption evaluation, Bioresource Technology 101 (2010) 4992-5002.
Junhua Zhang, et al., Isolation and characterization of wheat straw lignin with a formic acid process, Bioresource Technology 101 (2010) 2311-2316.
Anvar U. Buranov, et al., Isolation and characterization of lignins extracted from flax shives using pressurized aqueous ethanol, Bioresource Technology 101 (2010) 7446-7455.
Jagdish Raghani, et al., Combined Rapid-Steam Hydrolysis and Organosolv Pretreatment of Mixed Southern Hardwoods, Biotechnology and Bioengineering, vol. 33, pp. 681-686 (1989).
Xuejun Pan, et al., Biorefining of Softwoods Using Ethanol Organosolv Pulping: Preliminary Evaluation of Process Streams for Manufacture of Fuel-Grade Ethanol and Co-Products, Wiley Periodicals, Inc., 2005.

(Continued)

Primary Examiner — Elvis O Price
(74) Attorney, Agent, or Firm — Brouse McDowell, LPA; Jennifer L. Hanzlicek

(57) ABSTRACT

A method of production of value-added, biobased chemicals and derivative products from bioglycerin is described herein. The present method provides methods for desalinating, decolorizing, and concentrating bioglycerin for the production of biobased chemicals, derivative products, and/or purified bioglycerin.

51 Claims, 12 Drawing Sheets

(56) References Cited

OTHER PUBLICATIONS

Charles E. Wyman, et al., Comparative Sugar Recovery and Fermentation Data Following Pretreatment of Poplar Wood by Leading Technologies, American Institute of Chemical Engineers, 2009.

Lucian A. Lucia, et al., Chemicals and energy from biomass, Can. J. Chem. 84: 960-970 (2006).

M. Gonzalez Alriols, et al., Combined organosolv and ultrafiltration lignocellulosic biorefinery process, Chemical Engineering Journal 157 (2010) 113-120.

J.Y. Zhu, et al., Specific surface to evaluate the efficiencies of milling and pretreatment of wood for enzymatic saccharification, Chemical Engineering Science 64 (2009) 474-485.

European Parliament and of the Council, Promotion of the use of energy from renewable sources, Official Journal of the European Union, Apr. 2009.

John I. Zerbe, et al., Investigation of Fundamentals of Two-Stage, Dilute Sulfuric Acid Hydrolysis of Wood, 1987.

Verena Gehmayr, et al., New aspects of residual lignin isolation, Holzforschung, vol. 64, pp. 417-420, 2010.

Guoxiong Wu, et al., Improved Alkaline Oxidation Process for the Production of Aldehydes (Vanillin and Syringaldehyde) from Steam-Explosion Hardwood Lignin, Ind. Eng. Chem. Res. 1994, 33, 718-723.

Anderson Guerra, et al., Toward a Better Understanding of the Lignin Isolation Process from Wood, J. Agric. Food Chem. 2006, 54, 5939-5947.

Author Unknown, Lignin Isolation from Pulp.

Robert D. Perlack, et al., Biomass as Feedstock for a Bioenergy and Bioproducts Industry: The Technical Feasibility of a Billion-Ton Annual Supply, Apr. 2005.

Ian M. Morrison, Isolation and Analysis of Lignin-Carbohydrate Complexes from *Lolium multiflorum*, Phytochemistry, 1973, vol. 12, pp. 2979-2984.

United States Department of Agriculture, U.S. Biobased Products Market Potential and Projections Through 2025, Feb. 2008.

Jehad Saleh, et al., Glycerol removal from biodiesel using membrane separation technology, Fuel 89 (2010) 2260-2266.

Claudio J. A. Mota, et al., Glycerin Derivatives as Fuel Additives: The Addition of Glycerol/AcetoneKetal (Solketal) in Gasolines, Energy Fuels 2010, 24, 2733-2736.

Miller-Klein Associates, Impact of Biodiesel Production on the Glycerol Market, Oct. 2006.

E. Santacesaria, et al., New Process for Producing Epichlorohydrin via Glycerol Chlorination, Ind. Eng. Chem. Res. 2010, 49, 964-970.

Manuel Carmona, et al., Purification of glycerol/water solutions from biodiesel synthesis by ion exchange: sodium removal Part I, J. Chem. Technol. Biotechnol 2009; 84; 738-744, 2008.

Manuel Carmona, et al., Purification of glycerol/water solutions from biodiesel synthesis by ion exchange: sodium and chloride removal Part II, J. Chem. Technol. Biotechnol 2009; 84; 1130-1135, 2009.

Bryan Sims, Clearing the Way for Byproduct Quality, Biodiesel Magazine, Oct. 25, 2011.

Robert L. Stroup, Feedstock Considers for Future U.S. Producers, Biodiesel Magazine, Jan. 28, 2004.

Erin Voegele, London-based jatropha company goes public, Biodiesel Magazine, Nov. 29, 2011.

The National Biodiesel Board, US biodiesel industry sets new annual production record, Biodiesel Magazine, Nov. 28, 2011.

Office of the Biomass Program, U.S. Department of Energy, Multi Year Program Plan, 2007-2012, Aug. 31, 2005.

Author Unknown, Agricultural Residues Processing Pathway, Jul. 24, 2006.

Author Unknown, Chemicals from Biomass with Novel Tunable Solvents.

J Ragauskas, et al., The Path Forward for Biofuels and Biomaterials, Science 311, 484 (2006).

METHOD OF BIOBASED CHEMICAL PRODUCTION FROM CRUDE BIOGLYCERIN

I. BACKGROUND OF THE INVENTION

A. Field of Invention

The present invention is directed generally to a method of production of value-added, biobased chemicals, derivative products, and/or purified bioglycerin from bioglycerin. The present method described herein provides methods for desalinating, decolorizing, and/or concentrating bioglycerin for the production of biobased chemicals, derivative products, and/or purified bioglycerin.

B. Description of the Related Art

The world currently faces depletion of fossil fuels while demands for these fuels are ever increasing. Petrochemicals provide an energy source and a component of the majority of raw materials used in many industries. In fact, approximately 95% of all chemicals manufactured today are derived from petroleum. However, this heavy reliance upon fossil fuels is creating harm to the environment. The burning of these fossil fuels has led to the pollution of air, water and land, as well as global warming and climate changes. Through the use of fossil fuels, the environment has been harmed, perhaps irreparably, in an effort to meet the nearly insatiable demand for energy and manufactured products. Fossil fuels are a finite natural resource, with the depletion of readily available oil reserves across the globe; the supply chain has shifted to more complex and environmentally risky production technologies. A reduction and conservation of fossil fuels is clearly needed. Some alternatives to fossil fuels, like solar power, wind power, geothermal power, hydropower, and nuclear power, are used to a degree. However, a more efficient use of renewable resources is always being sought.

In particular, biofuels, which come from a renewable, carbonaceous source, are targeted to become one of these more efficient resources. In the demand for fossil fuels, biodiesel, a type of biofuel, has emerged as an environmentally friendly and potentially inexhaustible alternative to petroleum diesel, particularly during an oil crisis, a surge in crude oil prices or political unrest in the oil producing regions of the world. This renewable and clean-burning diesel replacement is said to reduce our dependence on foreign petroleum and create new employment within the green industry.

Biodiesel is considered as an environmentally friendly, renewable transportation and heating fuel relative to petroleum diesel. Biodiesel is made from agricultural oils and animal fats (or tallow). In addition, the triglyceride-rich waste streams of rendering and cooking operations find use in biodiesel production.

Biodiesel consists of mono-alkyl esters of long chain fatty acids that are produced by reaction of a triglyceride with an alcohol. This process yields biodiesel through a hydrolysis and/or transesterification reaction during which bioglycerin is cleaved as a by-product from the triglyceride. Thus, the process yields two products: biodiesel and crude bioglycerin. Crude bioglycerin is formed in approximately 1 part to each 10 parts of biodiesel. In the pure form, glycerin is a colorless, viscous liquid; however, crude bioglycerin may be a yellowish to dark brown liquid. It may be a clear to a turbid liquid, or have a syrup-like consistency. Crude bioglycerin may contain significant amounts of particulate matter, dissolved inorganic salts, alcohol and water, fatty acids and other impurities from the biodiesel process. Because of the high content of these impurities, uses for crude bioglycerin are limited while escalating global biodiesel production is culminating in a market glut for this by-product. Additionally, varying purity levels of the crude bioglycerin due to different feedstock sources of the biodiesel as well as different levels of in-process control among biodiesel producers do not provide a uniform approach to treating the bioglycerin. Even if the crude bioglycerin is treated, the purification of crude bioglycerin historically has been too expensive and commercial implementation of a crude bioglycerin purification process is yet to prove economical at large scale.

Because crude bioglycerin is expensive to purify and market demand for this material is limited, it is often sold at a significant discount relative to the price of petroleum-based glycerin. In lieu of a market outlet, crude bioglycerin would quickly accumulate as an unwanted waste product of biodiesel production with associated disposal costs. Although this green process of creating biodiesel fuel is grounded upon the sustainable use of renewable resources, the process unfortunately generates a low-value by-product that diminishes the overall green value of biodiesel production. However, a purified glycerin from the production of this biofuel would provide an even greener process as well as become a potential additional revenue stream for biodiesel producers. Such purified bioglycerin could compete and function as a green replacement to petroleum-derived glycerin and/or serve as a renewable feedstock for the production of value-added, derivative products, biobased chemicals, and/or purified bioglycerin.

In the pure form, glycerin has many uses. It is used in the food and beverage industry as a humectant, sweetener, solvent, preservative, filler, emulsifier, and thickening agent. It also has several uses in the personal care and pharmaceutical industries where it functions as a lubricant, humectant, laxative, bacteriostat, moisturizer and pharmaceutical excipient. It is a well-known component of glycerin soaps. It also has applications in tobacco, polyether polyols, alkyd resins, paints, coatings, lubricants, textiles, paper, biological research, fabric softeners, cellophane, explosives, and epoxy resins. Targeted emerging applications for glycerin include its conversion into commodity chemicals, like 1,2-propanediol and 1,3-propanediol, and into fine chemicals like epichlorohydrin, glycidyl ethers and glycidyl esters. Once implemented, these applications are expected to further improve global market demand for glycerin. Overall, a purified bioglycerin from biodiesel production could serve as a feedstock for production of value-added, biobased chemicals and as a means to reduce costs associated with waste stream disposal.

The present invention provides methods for purifying crude bioglycerin and converting bioglycerin into value-added, biobased chemicals while minimizing waste products.

II. SUMMARY OF THE INVENTION

Accordingly, it is an object of the invention to provide a method of biorefining. It may include the steps of providing a bioglycerin and treating the bioglycerin through one or more steps to provide a treated bioglycerin. The method may further include producing at least one derivative chemical product from the purified bioglycerin and/or treated bioglycerin.

One object of the present invention is that the purified bioglycerin may be provided from a by-product of biodiesel production.

Another object of the present invention is that the step of treating said bioglycerin to provide treated bioglycerin comprises at least one treatment of desalination treatment, decolorization treatment, and concentration treatment.

Yet another object of the present invention is that the desalination treatment provides desalinated bioglycerin, the decolorization treatment provides decolorized bioglycerin, and the concentration treatment provides concentrated bioglycerin.

Still another object of the present invention is that the step of treating a crude bioglycerin to provide a desalinated bioglycerin may use an ion exchange treatment.

Yet another object of the present invention is that the step of treating a crude bioglycerin to provide a decolorized bioglycerin can use a decolorizing treatment process.

Still yet another object of the present invention is that the step of treating a crude bioglycerin to provide a concentrated bioglycerin may use a concentration treatment process.

Still another object of the present invention is that the steps of desalination, decolorization, and concentration for purification of the crude bioglycerin may be performed in any order.

Yet another object of the present invention is that one or more of the steps of desalination, decolorization and concentration for purification of the crude bioglycerin can be skipped.

Still yet another object of the present invention is that the desalination step of the purification process may be performed under at least one condition of a batch flow condition and a continuous flow conditions.

According to one embodiment of the invention, a solvent can be added, recovered and recycled during the desalination treatment step of the crude bioglycerin purification process.

According to another embodiment of the invention, the ion exchange resins may be regenerated and recycled during the desalination step of the purification process.

According to still another embodiment of the invention, the desalination step of the purification can be low energy demanding.

According to still yet another embodiment of the invention, the desalination step of the crude bioglycerin can recover salt, which is useful for commercial de-icing or lowering the freezing point of solutions.

According to still yet another embodiment of the invention, the desalination step of the purification process produces water and/or an organic solvent that may be recovered and reused.

Still another object of the invention is that the decolorization step of the crude bioglycerin purification process may be performed under batch or continuous flow conditions.

According to one embodiment of the invention, an organic solvent may be recovered and recycled during the decolorization step of purification process.

According to still another embodiment of the invention, the decolorization step of purification process may use activated charcoal.

According to another embodiment of the invention, the decolorization step of purification process can be low energy demanding.

Still another object of the invention is that the concentration step of purification process can be performed under at least one condition of a batch flow condition and a continuous flow conditions.

According to one embodiment of the invention, the concentration step of the purification process can be performed at reduced pressure and modest temperature.

According to another embodiment of the invention, the concentration step of the purification process can be low energy demanding.

Another object of the invention is that the yield recovery of the purified bioglycerin from the purification process may be greater than 80% of the theoretical yield amount of bioglycerin from biodiesel production.

Yet another object of the invention is the yield recovery of the purified bioglycerin from the purification process can be greater than 90% of the theoretical yield amount of bioglycerin from biodiesel production.

Still another object of the invention is that the weight of the purified bioglycerin from the crude glycerin purification process may be greater than 80% of the weight of the crude bioglycerin.

Still yet another object of the invention is that the weight of the purified bioglycerin from the purification process can be greater than 90% of the weight of the crude bioglycerin.

Still yet another object of the invention can be the production of one or more derivative chemical products from the crude bioglycerin or purified bioglycerin.

According to one embodiment of the invention, purified bioglycerins of different purities can produce one or more derivative chemical products.

According to another embodiment of the invention, the production of derivative chemical products from the crude bioglycerin or purified bioglycerin may take place by a chemical process.

According to still another embodiment of the invention, the production of derivative chemical products from the crude bioglycerin or purified bioglycerin may take place by a biological process.

According to yet another embodiment of the invention, the production of derivative chemical products from the crude bioglycerin or purified bioglycerin may take place by a catalytic process.

According to still yet another embodiment of the invention, the production of derivative chemical products from the crude bioglycerin or purified bioglycerin may take place by pyrolytic process According to yet another embodiment of the invention, the production of derivative chemical products from the crude bioglycerin or purified bioglycerin can involve one or more chemical, biological, catalytic, or pyrolysis processes.

Further, another object of the present invention can be functionalizing the crude bioglycerin or purified bioglycerin prior to the production of derivative chemical products.

According to another aspect of the invention, the desalination process may yield a plurality of derivative products comprising purified glycerin and glycerin derivatives, C2/C3 alcohols, C2/C3 diols, C2/C3 aldehydes/ketones, C2/C3 carboxylic acids, C5/C6 polyols and polyol derivatives, glycidol and glycidyl derivatives, glyceraldehyde and glycerin derivatives, and epihalohydrins from the crude bioglycerin or purified bioglycerin.

According to yet another aspect, the invention can provide for the production of a plurality of derivative chemicals, including achiral, racemic and optically pure products, comprising of ethanol; ethylene glycol; acetaldehyde; glyoxal; acetic acid; glycolic acid; glyoxylic acid; oxalic acid; n-propanol; isopropanol; 1,2-propanediol; 1,3-propanediol; acetone; 1-hydroxyacetone; 1,3-dihydroxyacetone; propionic acid; lactic acid; pyruvic acid; malonic acid; hydroxymalonic acid; high purity glycerin; functionalized glycerins like 4-(hydroxymethyl)-1,3-dioxolan-2-one, 4-methyl-1,3-dioxolane, (2,2-dimethyl-1,3-dioxolan-4-yl)methanol and 1,4-dioxaspiro[4.5]decane-2-methanol; glyceraldehyde; functionalized glyceraldehydes like 2,2-dimethyl-1,3-dioxolane-4-carbaldehyde and 1,4-dioxaspiro[4.5]decane-2-carbaldehyde; glycidol; glycidyl ethers like glycidyl methyl ether, glycidyl isopropyl ether, glycidyl n-butyl ether, glycidyl tert-butyl ether, glycidyl allyl ether, glycidyl propargyl ether, glycidyl hexadecyl ether, glycidyl octyl/decyl ether, glycidyl phenyl ether and glycidyl benzyl ether; glycidyl esters like 2-oxiranylmethyl formate, glycidyl butyrate, glycidyl acrylate, glycidyl methacrylate, diglycidyl 1,2-cyclohexanedicarboxylate, glycidyl benzoate and glycidyl 4-nitrobenzoate; epichlorohydrin; epibromohydrin; and polyols like ribitol, arabitol, xylitol, mannitol, sorbitol, galactitol, allitol, and iditol from the crude bioglycerin or purified bioglycerin.

Yet another object of the invention is that it can provide a method of biorefining, comprising the steps of providing a crude bioglycerin, treating crude bioglycerin by one or more desalination, decolorization and concentration treatment processes to provide a purified bioglycerin, and producing a plurality of derivative chemical products from the purified bioglycerin.

Still yet another object of the present invention is that the can provide for a production of derivative products that can be used in the production of other chemicals, products, and materials.

Still another object of the invention is that it can provide a method of biorefining. It may include the steps of providing a crude bioglycerin and treating crude bioglycerin to provide a purified bioglycerin. The method may further include recovering and using the salts, water, and alcohol contaminating crude bioglycerin from the biodiesel production process.

Yet another object of the invention is that it can provide a method of biorefining. It may include the steps of providing a crude bioglycerin and treating crude bioglycerin by one or more treatments of the desalination treatment, the decolorization treatment, and the concentration treatment to provide a purified bioglycerin and producing a plurality of biobased chemicals, derivative products, and/or purified glycerin from the crude bioglycerin and/or a purified bioglycerin. The method may further include recovering and recycling any solvents used in the purification of crude bioglycerin.

Still yet another object of the invention is that it may provide a method of providing a crude bioglycerin and treating crude bioglycerin to provide a purified bioglycerin where the waste product from the purified bioglycerin process can be used to produce energy.

Further, another object of the present invention can be to provide a method for biorefining that is easy to implement and use.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof, and wherein.

IV. DETAILED DESCRIPTION OF THE INVENTION

Figure 1:
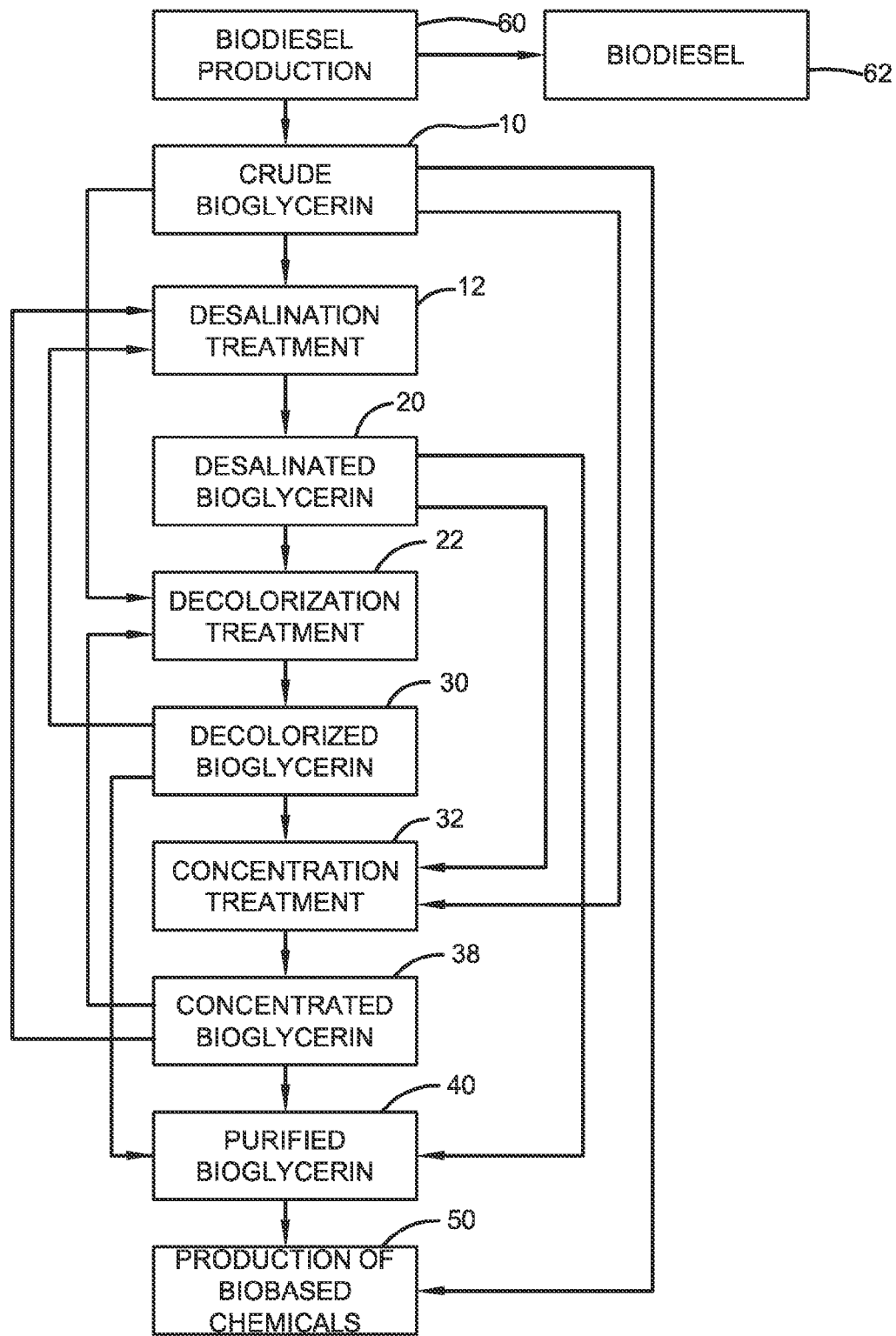
FIG. 1 is a flow diagram schematically illustrating the present invention.

Referring now to the drawings wherein the showings are for purposes of illustrating embodiments of the invention only and not for purposes of limiting the same. Relative language used herein is best understood with reference to the drawings, in which like numerals are used to identify like or similar items.

FIG. 1 shows the overall process of converting a crude bioglycerin 10 into a purified bioglycerin 40, and further in the production of biobased chemicals 50. It is a summary of the multiple pathways to process and use crude bioglycerin 10 as a renewable, carbonaceous material for the production of biobased chemicals 50.

Crude bioglycerin 10 is a by-product of biodiesel production 60, through the hydrolysis and/or transesterification process used in the manufacture of biodiesel 62. Biodiesel production 60 yields mostly biodiesel 62, with roughly 10% of the product mass being a crude bioglycerin 10. Escalating biodiesel production 60 across the globe is generating large quantities of crude bioglycerin 10 that could be used in the production of biobased chemicals 50.

Crude bioglycerin 10 can contain several impurities from the hydrolysis and/or transesterification process used in the manufacture of biodiesel 62. Such impurities can include an alcohol like methanol or ethanol, and water. The presence of the alcohol in crude bioglycerin 10 may be due to the fact that an excess of this alcohol can be used to drive the hydrolysis and/or transesterification process to completion. Also, different manufacturers may recover the alcohol to varying extents, producing an inconsistent crude bioglycerin 10. In addition to the alcohol and water impurities, the crude bioglycerin 10 may contain dissolved salts, like sodium chloride or sodium sulphate or potassium chloride or potassium sulphate. These salts may arise from neutralization of the transesterification and/or hydrolysis process. Furthermore, the crude bioglycerin 10 may contain residual fatty acids and other organic impurities leading to color. These impurities may result from either incomplete biodiesel production 60 or the lipid feedstock entering the refinery. The levels of water and alcohol contamination in crude bioglycerin 10 may be controlled by evaporation/distillation or by implementing tighter control of the biodiesel processing parameters. However, the salts, which may amount to about 4-10% of the crude bioglycerin 10, can be more challenging to remove. Further these salts may impede transformations of the crude bioglycerin 10 into the purified bioglycerin 40 or the production of biobased chemicals 50.

Because of these impurities, there is limited market demand for crude bioglycerin 10 and the market that does exist often commands a price as low as $\frac{1}{10}^{th}$ that of petroleum glycerin. The reason is that these impurities, and in particular the salts, severely hamper or restrict uses of crude bioglycerin 10. Historically, purification of the crude bioglycerin 10 has proven too expensive for commercial implementation. For example, the purification of bioglycerin by distillation is a very energy demanding process because the boiling point of glycerin is 290° C. (554° F.). However, the process in FIG. 1 provides a low energy, self-contained process that can remove both the salts and other impurities from the crude bioglycerin 10. The process shown in FIG. 1 can operate as a stand-alone biorefinery receiving the crude bioglycerin 10 for production of biobased chemicals 50, or it can provide an additional on-site option to a biodiesel manufacturer for waste stream reduction and/or value-added products production.

During biodiesel production 60, the crude bioglycerin 10 may have an inconsistent appearance from batch to batch or from producer to producer. These differences in appearance are typically associated with the characteristics of different triglyceride streams coming into these biodiesel facilities, and/or differences in the processes and manufacturing controls across different biodiesel facilities. The crude bioglycerin 10 obtained from biodiesel production 60 can appear as a golden or slightly yellow liquid, or a dark brown substance that has a liquid to a syrup-like character. The crude bioglycerin 10 can be translucent or turbid in appearance. Depending on the condition of the crude bioglycerin 10, several steps within the process of FIG. 1 can be carried out to produce a purified bioglycerin 40 and/or for the production of biobased chemicals 50. These processes can be tailored to meet the end product requirements for a purified bioglycerin 40 and/or the raw material specification requirements for production of biobased chemicals 50.

Depending on the condition of the crude bioglycerin 10, it may need to be subjected to the desalination treatment 12, the decolorization treatment 22, and/or the concentration treatment 32. These processing treatments required for purifying the crude bioglycerin 10 depend on the end product requirements for the purified bioglycerin 40 and/or the raw material specification requirements for the production of biobased chemicals 50 from a purified bioglycerin 40.

For instance, if the crude bioglycerin 10 from the biodiesel production 60 requires desalination, it may undergo a desalination treatment 12 to become desalinated bioglycerin 20. Because these salts can interfere with the purified bioglycerin 40 in the production of biobased chemicals 50, a desalination treatment 12 step is used to remove these impurities in order to provide a desalinated bioglycerin 20. The desalination treatment 12 step is further detailed in FIG. 2. The desalinated bioglycerin 20 may then go through a decolorization treatment 22 to obtain a decolorized bioglycerin 30 if a lighter color material is needed. The decolorization treatment 22 reduces the level of residual fatty acid and other colored organic impurities in the material. The decolorization treatment 22 step is further detailed in FIG. 8. The decolorized bioglycerin 30 may then undergo a concentration treatment 32 wherein further the alcohol and water impurities are removed to provide a concentrated bioglycerin 38. The concentration treatment 32 step is detailed in FIG. 9. After the concentration treatment 32 step is complete, a purified bioglycerin 40 is produced. If desired, the purified bioglycerin 40 can then be transformed into derivative products such as commodity, fine, and/or specialty chemicals through a production of biobased chemicals 50 step or it can be further purified. For this process, the purification of crude bioglycerin 10 does not have to begin with the desalination treatment 12. The purification process may start with the desalination treatment 12, the decolorization treatment 22, or the concentration treatment 32, or it can proceed directly to the production of biobased chemicals 50.

Within the overall process of converting the crude bioglycerin 10 into a purified bioglycerin 40 and/or the production of biobased chemical products 50, several steps may be omitted if the crude bioglycerin 10 does not require desalination, decolorization, and/or concentration to achieve the end product specification for the purified bioglycerin 40 and/or the production of biobased chemicals 50. Depending on the condition of the intermediate bioglycerin product during any step of the process shown in FIG. 1, a determination of whether the material needs to undergo a further treatment can be made. For example, the crude bioglycerin 10 may be subjected to a desalination treatment 12 to remove the salt impurities. If the crude bioglycerin 10 does not require desalination, the desalination treatment 12 can be skipped and crude bioglycerin 10 may then be sent to a decolorization treatment 22 to improve its color. If desalination is required at this point, the decolorized bioglycerin 30 can then be subjected to a desalination treatment 12 to remove the salt impurities. If no desalination is needed, then the 14 decolorized bioglycerin 30 can either go through a concentration treatment 32, or it can be directed converted into a purified bioglycerin 40. Alternatively, crude bioglycerin 10 may directly be sent to a concentration treatment 32 for production of a concentrated bioglycerin 38, which may be converted into either a purified bioglycerin 40 and/or sent for the production of biobased chemicals 50 if neither desalination nor decolorization is required. In other instances, the crude bioglycerin 10 may omit the desalination treatment 12, the decolorization treatment 22, and the concentration treatments 32 and be directly converted into derivative products such as commodity, fine and/or specialty chemicals with the production of biobased chemicals 50 step.

After the desalination treatment 12, the desalinated bioglycerin 20 may be sufficiently treated to become a purified bioglycerin 40 if the specification requirements are met for a purified bioglycerin 40 and/or the production of biobased chemicals 50. Alternatively, if additional processes are needed for the desalinated bioglycerin 20 but not the decolorization treatment 22, then the desalinated bioglycerin 20 may be sent to a concentration treatment 32 where it becomes a concentrated bioglycerin 38, which can be used for the conversion to a purified bioglycerin 40 or sent for the production of biobased chemicals 50.

Additionally, the concentrated bioglycerin 38 may also be processed to a purified bioglycerin 40, or undergo either desalination treatment 12 or decolorization treatment 22 before it can be used for the conversion to a purified bioglycerin 40 and/or sent for the production of biobased chemicals 50.

One detail to note during these processes is that the summary of the pathway shown in FIG. 1 may be changed to include a different order for the processes. This is designated by the additional arrows that demonstrate that the final product may not be dependent upon a particular order of the treatments, but rather which treatments can be applied and what processes may be required for the desired end product. This difference in order may be needed due to processing limitations or discoveries with respect to what may be required to meet the specifications of the end product or intended use in the production of biobased chemicals 50.

Also, any of the process treatment steps like the desalination treatment 12, the decolorization treatment 22, or the concentration treatment 32, may be repeated to provide the requirements for a purified bioglycerin 40 and/or the production of biobased chemicals 50.

Furthermore, any of the process treatment steps like the desalination treatment 12, the decolorization treatment 22, or the concentration treatment 32, may be conducted under batch or flow conditions for the production of the purified bioglycerin 40 and/or the production of biobased chemicals 50.

The processing outlined in FIG. 1 can also address problems with processing crude bioglycerin 10 without the need to invest large amounts of capital in expensive processing equipment to purify this by-product of biodiesel production 60.

The processing outlined in FIG. 1 can further avoid the high costs of purifying crude bioglycerin 10 by conventional means in that the process in FIG. 1 can be low energy and self-contained.

Figure 2:
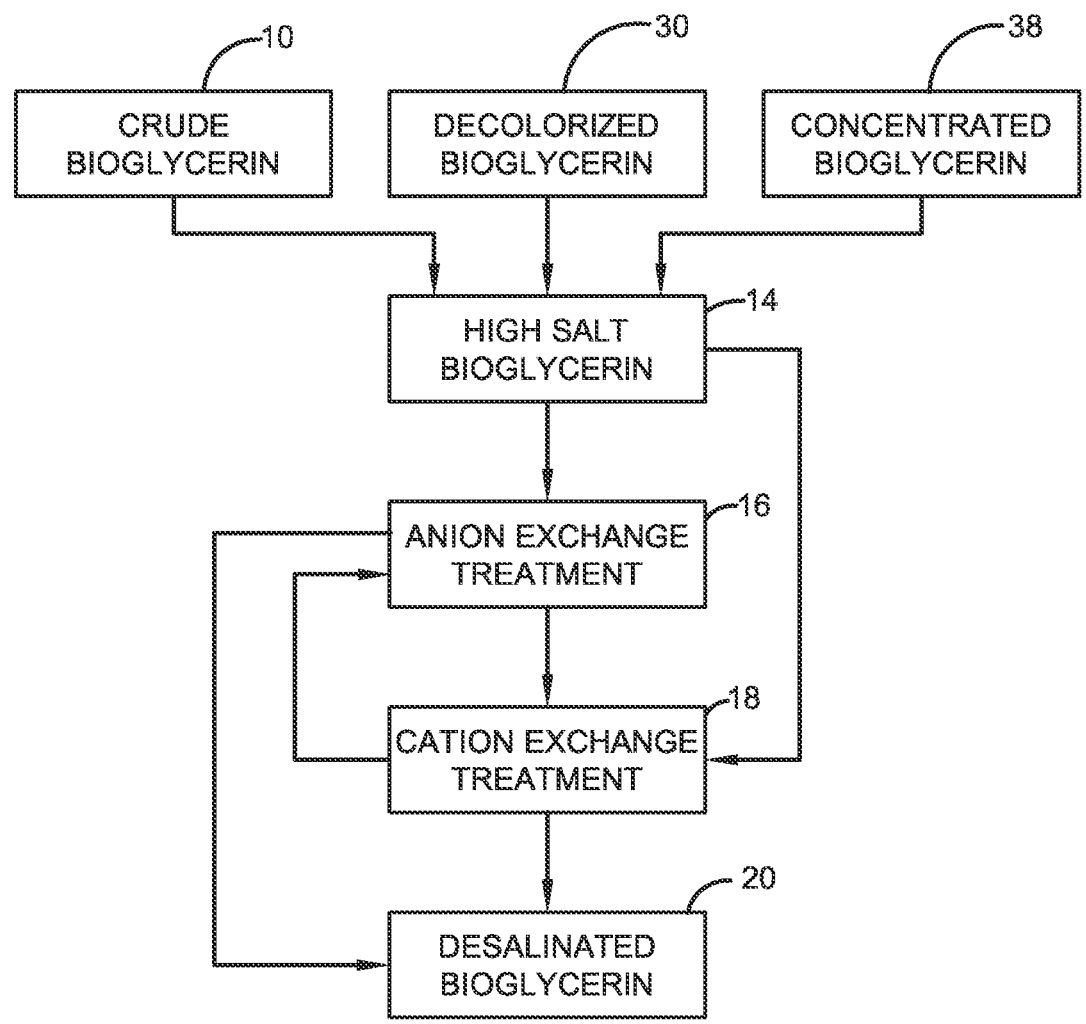
FIG. 2 is a flow diagram schematically illustrating another aspect of the present invention.

FIG. 2 illustrates a process for the desalination treatment 12 in which a high salt bioglycerin 14 may be transformed into a desalinated bioglycerin 20. This desalination process may occur through ion exchange to remove the salt impurities. The ion exchange treatment or process can be a two-stage process consisting of both an anion exchange treatment 16 and a cation exchange treatment 18. This two-step, ion exchange treatment can utilize both anion exchange resins and cation exchange resins to purify the high salt bioglycerin 14 by acting to exchange the ions that contribute to the salt impurities of the high salt bioglycerin 14. Anions are atoms or groups of atoms that have gained electrons, and are therefore negatively charged. Cations are atoms or groups that have lost an electron to become positively charged. Together, anions and cations form salts like sodium chloride or sodium sulphate or potassium chloride or potassium sulphate. Anion exchange resins and cation exchange resins can be both selective and versatile, where specific types of ions can be removed from a material depending on the specific anion exchange treatment 16 and cation exchange treatment 18 chosen.

First, the high salt bioglycerin 14 may be received. The high salt bioglycerin 14 can originate from a crude bioglycerin 10, a decolorized bioglycerin 30, and/or a concentrated bioglycerin 38. The high salt bioglycerin 14 may then undergo an anion exchange treatment 16. The anion exchange treatment 16 step can serve to reduce or remove the anionic impurities present in high salt bioglycerin 14 by use of an anion exchange resin, which exchanges the negatively charged ions of the salt impurities with the counterion bound to the resin. For instance, this anion exchange treatment 16 may remove halide, sulphate and other anions first from the high salt bioglycerin 14 and replace those anions with hydroxide anions. Through the anion exchange treatment 16, the anionic components of the salt impurities can be removed from the high salt bioglycerin 14. After the anion exchange treatment 16 step is completed, a cation exchange treatment 18 step may then occur to reduce and replace the cations from the salt impurities present in the high salt bioglycerin 14 with the counterion ion bound to the cation exchange resin, typically a proton. Through the cation exchange treatment 18, the cationic components of the salt impurities may be reduced and removed from the high salt bioglycerin 14. For example, this cation exchange treatment 18 may remove sodium, potassium and other cations and replace those cations with protons. Therefore, through both anion and cation exchange treatment steps, the high salt bioglycerin 14 can be reduced in levels of both positively and negatively charged ionic salt impurities, and the desalinated bioglycerin 20 may now be formed. The desalinated bioglycerin 20 may then go through one or more additional treatments of decolorization, concentration, and/or transfer to the production of purified bioglycerin 40 and/or biobased chemical product as described in FIG. 1. In the course of the desalination treatment 12, water can be produced as a by-product through a combination of the hydroxide anions derived from the anion exchange treatment 16 step with the protons derived from the cation exchange treatment 18 step. To reduce waste streams, this water may be recovered and reused in the desalination treatment 12.

Although the desalination treatment 12 in which the high salt bioglycerin 14 is transformed into a desalinated bioglycerin 20 can be achieved by first subjecting the high salt bioglycerin 14 to an anion exchange treatment 16 step and following that step with a cation exchange treatment 18 step, the process is not limited to this order of ion exchange treatments. Instead, the high salt bioglycerin 14 can first undergo a cation exchange treatment 18, and followed by an anion exchange treatment 16. In other words, either ion exchange treatment can be used first.

Alternatively, an amphoteric exchange treatment could be used instead wherein both an anion exchange treatment 16 and a cation exchange treatment 18 occur at once. This type of amphoteric exchanger will exchange both cations and anions simultaneously. Instead of completing two different steps where the anion exchange treatment 16 step and the cation exchange treatment 18 step are separate, a process where all of the ion exchanging can occur in a condensed step may also be used.

Moreover in the course of the desalination treatment 12, each of the steps of anion exchange treatment 16 and cation exchange treatment 18 may be conducted more than one time. Repeating the anion exchange treatment 16 step and/or cation exchange treatment 18 step can allow for applications wherein the levels of dissolved salts in desalinated bioglycerin 20 or purified bioglycerin 40 may be further reduced, especially if required for certain specifications of intended product use.

The reduction in levels of both positively and negatively charged ions in the desalination treatment 12 may lead to the formation of a desalinated bioglycerin 20 since the salt impurities are reduced or removed by the ion exchange treatment or process. With the desalination treatment 12 of the high salt bioglycerin 14, both the possibility of creating value-added products and the prevention of a costly waste stream may provide incentives for utilizing the desalination treatment 12 process.

Figure 3:
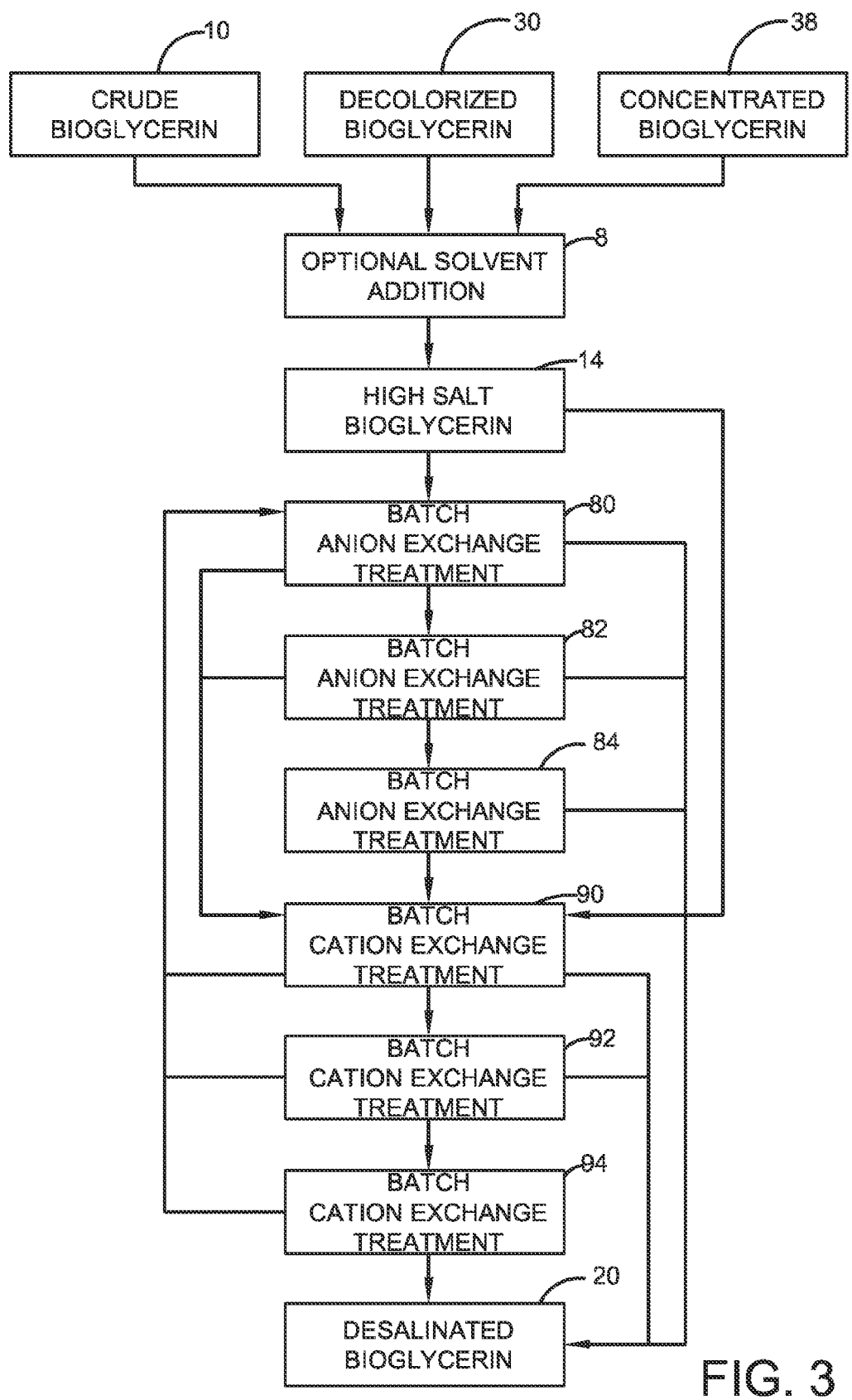
FIG. 3 is a flow diagram schematically illustrating another aspect of the present invention.

In FIG. 3, a detailed batch purification method for the desalination treatment 12 of the high salt bioglycerin 14 is shown. During this batch process, the high salt bioglycerin 14 can be converted into a desalinated bioglycerin 20. The ion exchange treatment or process may be done through multiple anion exchange and cation exchange treatments. These anion and cation exchange treatments typically employ an ion exchange resin to remove the negatively charged and positively charged ions that are present in the salt impurities of the high salt bioglycerin 14.

Ion exchange resins are classified as cation exchangers, which contain positively charged mobile ions available for exchange, and anion exchangers, whose exchangeable ions are negatively charged. Both anion and cation exchange resins may be produced from the same basic organic polymers. These resin types differ in the ionizable group attached to the organic polymer network. It is this functional group that determines the chemical behaviour of the resin. Ion exchange resins can be broadly classified as strong or weak acid cation exchangers, or strong or weak base anion exchangers. Ion exchange resins are insoluble substances containing loosely bound counterions that are able to be exchanged with other ions in solutions that come into contact with the resin. These exchanges take place without any physical alteration to the ion exchange material other than the exchange of the loosely bound counterions.

Figure 6:
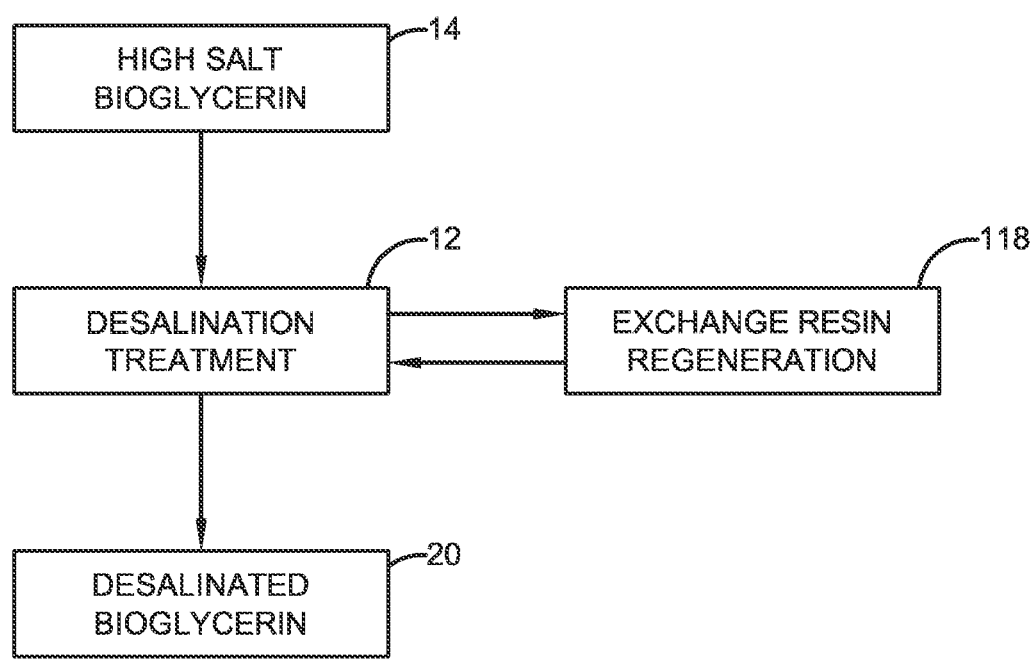
FIG. 6 is a flow diagram schematically illustrating another aspect of the present invention.
Figure 7:
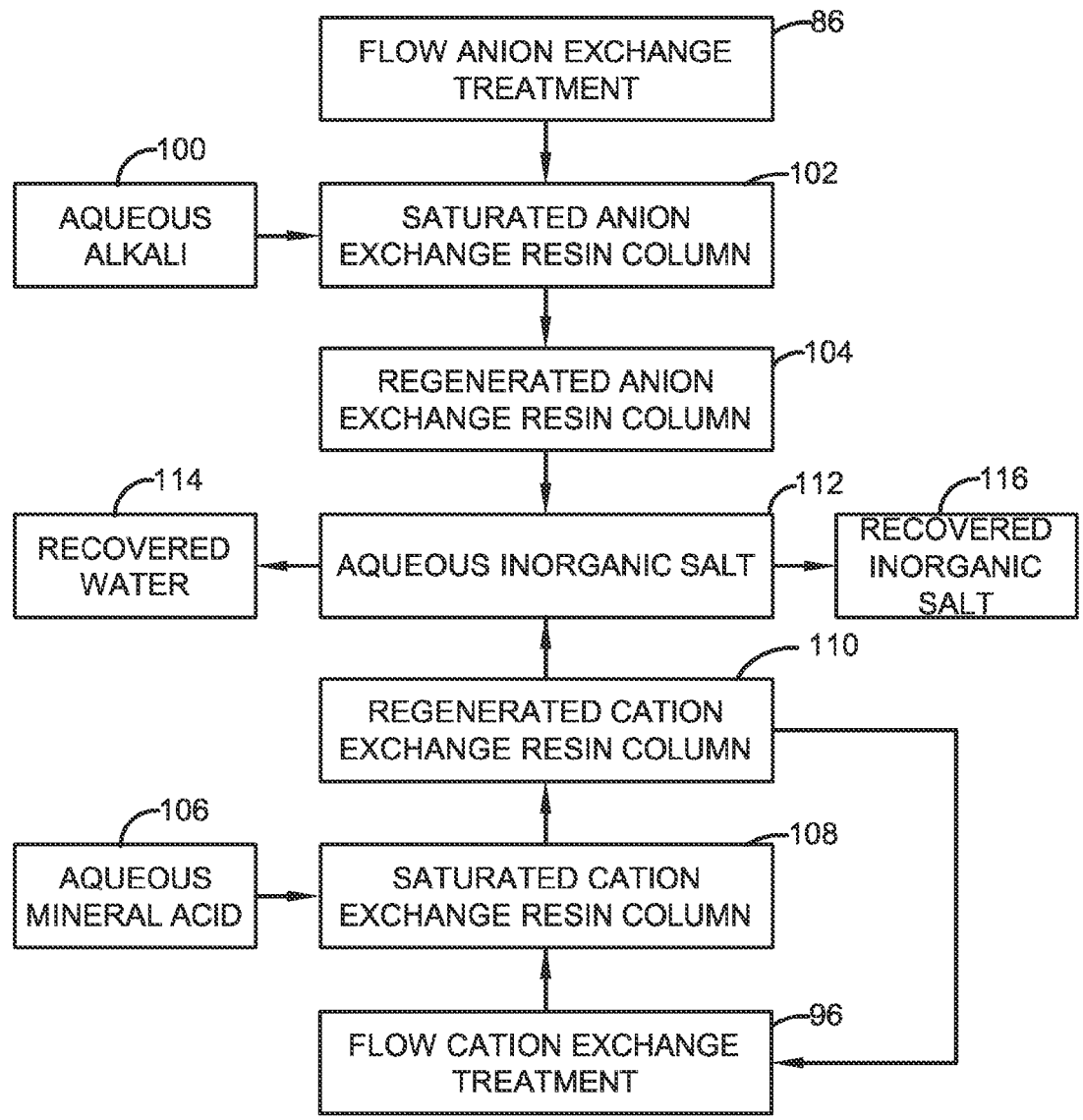
FIG. 7 is a flow diagram schematically illustrating another aspect of the present invention.

For the anion exchange treatment 16 and the cation exchange treatment 18 of high salt bioglycerin 14, two different purification methods can be used: batch purification and continuous flow purification. In both instances, the high salt bioglycerin 14 would be subjected to ion exchange resins. Batch purification allows for purification in discrete batches. Batch purification is especially advantageous where different end products are needed. Continuous flow purification provides processing in a continuous flow, and allows for an increased production of a particular end product. A batch purification method is shown in FIG. 3. A continuous flow purification method is outlined in FIG. 4. There are, however, different modifications that must be considered in determining which purification method to use. In the batch purification method, the ion exchange resin is isolated by filtration before regeneration. This regeneration process for the batch purification method is illustrated in FIG. 6. Unlike the batch purification method, the continuous flow purification method regenerates the ion exchange resin within a column, as shown in FIG. 7. No matter which method is utilized, either method will provide the desalinated bioglycerin 20.

Returning now to FIG. 3, the high salt bioglycerin 14 can be received in the batch purification method for the desalination treatment 12. The high salt bioglycerin 14 may originate from a crude bioglycerin 10, a decolorized bioglycerin 30, and/or a concentrated bioglycerin 38. As the crude bioglycerin 10, decolorized bioglycerin 30 and/or concentrated bioglycerin 38 may be brought together as the high salt bioglycerin 14; an optional solvent addition 8 can be done. This optional solvent addition 8 can be water, an alcohol like methanol or ethanol or an alcohol/water mixture. This optional solvent addition 8 can serve to reduce the viscosity of the high salt bioglycerin 14 and help enhance recovery of the desalinated bioglycerin 20 from the ion exchange resins. Solvents used in the optional solvent addition 8 may be recovered in the concentration treatment 32, as shown in FIG. 1.

For FIG. 3, the high salt bioglycerin 14 may be subjected to multiple treatments with both anionic and cationic ion exchangers in order to produce the desalinated bioglycerin 20. The flow path for the ion exchange treatments can depend upon the anion and cation level specifications for production of either the desalinated bioglycerin 20 or the purified bioglycerin 40 for the production of biobased chemicals 50. Although FIG. 3 provides a general flow in the production of a desalinated bioglycerin 20, the process may instead provide a purified bioglycerin 40 for the production of biobased chemicals 50. A general flow is outlined in FIG. 3, but any of the exchange treatments may be repeated or skipped altogether, depending on the requirements and product specifications for the intended use. Additionally, FIG. 3 shows a batch flow that is first subjected to anion exchange treatments and is then subjected to cation exchange treatments. However, the cation exchange treatments may be conducted before the anion exchange treatments if the material requires this process or if the batch process desalination treatment 12 is set-up to process the high salt bioglycerin 14 with the batch cation exchange treatments first.

The batch purification method outlined in FIG. 3 shows a series of both anion and cation exchange treatments. The batch anion exchange treatment 80 may occur first. In a basic anion exchange resin treatment, the resin can reduce or remove halide, sulphate and other anions that are present as impurities in the high salt bioglycerin 14 and instead replace those anions by the counterion bound to the anion exchange resin, typically hydroxide anions. A second and third anion exchange treatment, batch anion exchange treatment 82 and batch anion exchange treatment 84, may then occur. The purpose of second and third batch anion exchange treatments can be to further reduce the respective anion impurity levels of the product to specification for a desalinated bioglycerin 20 and/or a purified bioglycerin 40 for the production of biobased chemicals 50. Depending upon the resin, the anion exchange resin can be regenerated with an alkali base like aqueous sodium hydroxide or potassium hydroxide after the anion exchange treatment 82. This resin regeneration process is detailed further in FIGS. 6 and 7.

The batch cation exchange treatment 90 may then occur after the anion exchange treatment(s). In a cation exchange resin treatments, the resin may reduce or remove sodium, potassium and other cations from the impurities present in the high salt bioglycerin 14 and replace those cations by the counterion bound to the cation exchange resin, typically protons. The high salt bioglycerin 14 may then undergo a second and third cation exchange, batch cation exchange treatment 92 and batch cation exchange treatment 94. Like the anion exchange treatment process, the purpose of the second and third batch cation exchange treatments can be to further reduce the respective cation levels of the product to specification for a desalinated bioglycerin 20 and/or a purified bioglycerin 40 for the production of biobased chemicals 50. Depending on the resin, the cation exchange resin can be regenerated with acids like aqueous hydrochloric acid or sulphuric acid, as detailed further in FIGS. 6 and 7.

Besides the resin regeneration that provides a greener and less costly means of desalinating the high salt bioglycerin 14, the batch purification method of FIG. 3 also can potentially generate both salt and water as recoverable by-products. This process is detailed further in FIGS. 5 and 7.

Figure 4:
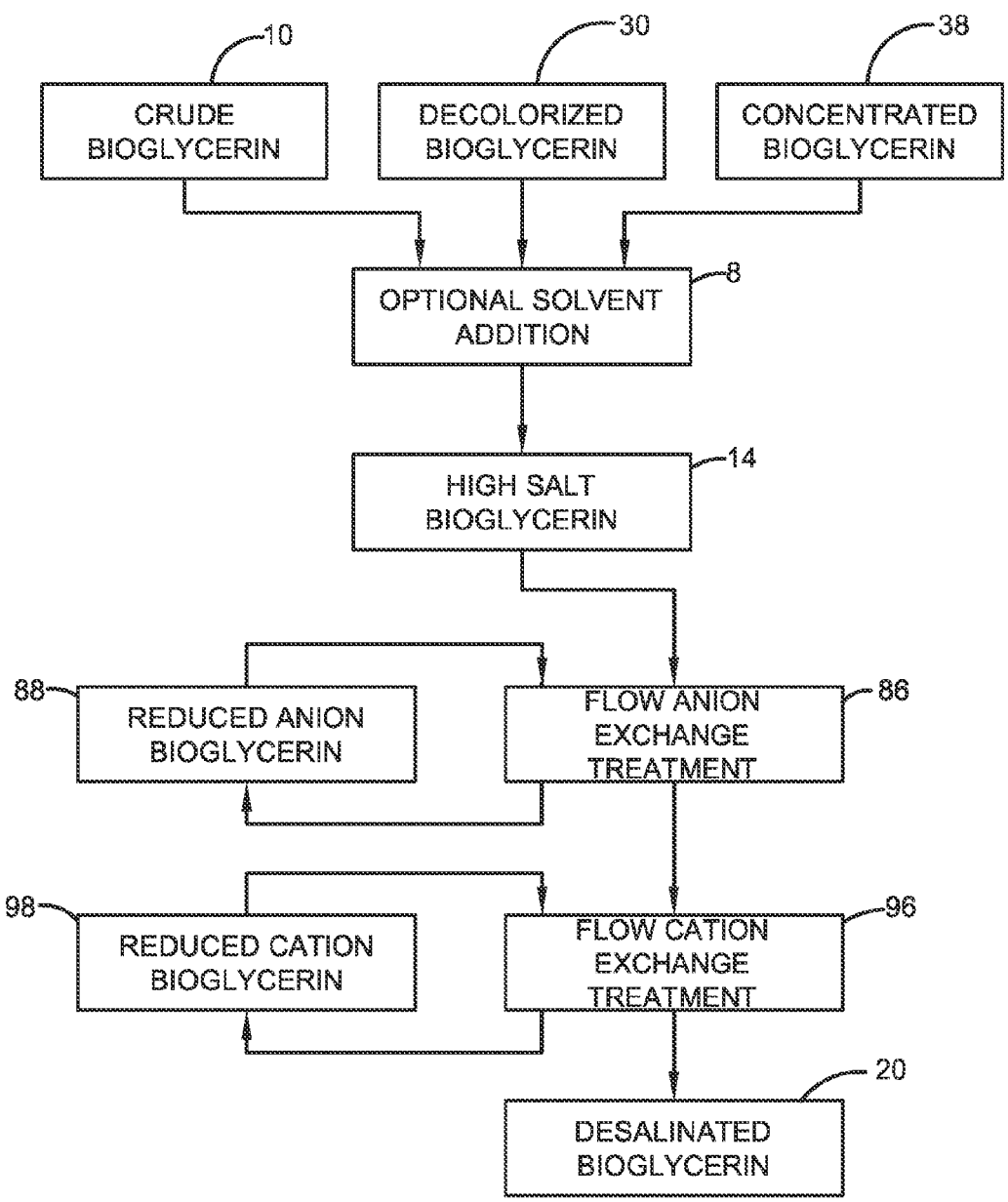
FIG. 4 is a flow diagram schematically illustrating another aspect of the present invention.

In FIG. 4, a detailed continuous flow purification method for the desalination treatment 12 of the high salt bioglycerin 14 is shown. During this continuous flow process, the high salt bioglycerin 14 can be converted into a desalinated bioglycerin 20. The ion exchange treatment may be done through multiple anion exchange and cation exchange treatments. These anion and cation exchange treatments typically employ an ion exchange resin to remove the negatively charged and positively charged ionic impurities present in the high salt bioglycerin 14.

First, the high salt bioglycerin 14 may be received in the continuous flow purification method for desalination treatment 12. The high salt bioglycerin 14 can originate from a crude bioglycerin 10, a decolorized bioglycerin 30, and/or a concentrated bioglycerin 38. As the crude bioglycerin 10, decolorized bioglycerin 30 and/or concentrated bioglycerin 38 may be brought together as the high salt bioglycerin 14; an optional solvent addition 8 can be done. This optional solvent addition 8 can be water or an alcohol like methanol or ethanol or a water/alcohol mixture. This optional solvent addition 8 serves to reduce the viscosity of the high salt bioglycerin 14 and helps enhance recovery of the desalinated bioglycerin 20 from the ion exchange resins. Solvents used in the optional solvent addition 8 may be recovered in the concentration treatment 32, as shown in FIG. 1.

Like the batch purification method in FIG. 3, the high salt bioglycerin 14 of FIG. 4 may be subjected to multiple treatments with both anionic and cationic ion exchangers in order to produce the desalinated bioglycerin 20. The flow path for the ion exchange treatments depends upon the anion and cation level specifications for the production of either a desalinated bioglycerin 20 and/or a purified bioglycerin 40 for the production of biobased chemicals 50. Although FIG. 4 provides a general flow in the production of a desalinated bioglycerin 20, the process may instead lead to a purified bioglycerin 40 for the production of biobased chemicals 50.

The general flow outlined in FIG. 4 shows a continuous flow process that can be first subjected to flow anion exchange treatments 86, and is then subjected to flow cation exchange treatments 96. However, the cation exchange treatments may be conducted prior to the anion exchange treatments if the material requires this desalination process or if the continuous flow process desalination treatment 12 is set-up to process the high salt bioglycerin 14 with the cation exchange treatments first.

Optionally, the flow anion exchange treatment 86 may be subjected to one or more reduced anion bioglycerin 88 treatments. These treatments are optional cycle(s) of flow anion exchange where the reduced anion bioglycerin 88 can be sent through the flow exchange column again to further reduce anion levels to the desired specifications for the production of the desalinated bioglycerin 20, and/or a purified bioglycerin 40 and/or be sent for the production of biobased chemicals 50.

Also, the reduced cation bioglycerin 98 may be optionally subjected to one or more cycles(s) of the flow cation exchange treatment 96 in order to meet the cation levels to the desired specifications for the production of the desalinated bioglycerin 20, and/or a purified bioglycerin 40 and/or be sent for the production of biobased chemicals 50. Like the flow cation exchange treatment 96 of the reduced anion bioglycerin 88, the reduced cation bioglycerin 98 can be subjected to optional cycle(s) of the flow cation exchange treatment 96.

Depending upon the resin, the anion exchange resin can be regenerated with an alkali base like aqueous sodium hydroxide or potassium hydroxide, and the cation exchange resin can be regenerated with acids like aqueous hydrochloric acid or sulphuric acid after the continuous flow exchange process. Besides the resin regeneration that provides a greener and less costly means of desalinating the high salt bioglycerin 14, the continuous flow purification method of FIG. 4 also can potentially generate both salt and water as recoverable by-products. This process is detailed further in FIGS. 5 and 7.

Figure 5:
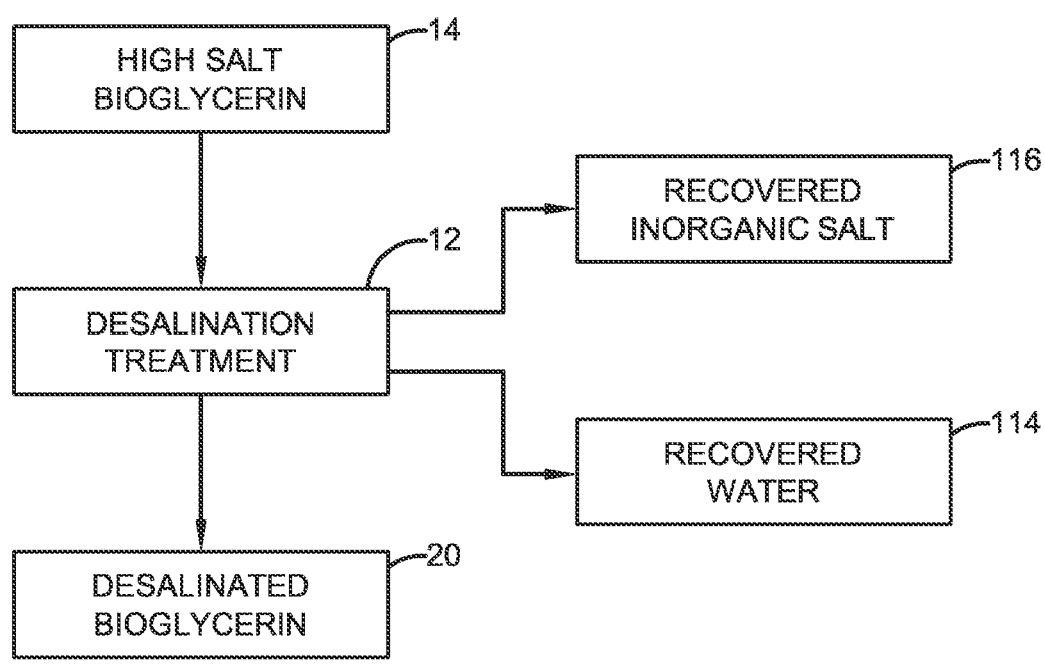
FIG. 5 is a flow diagram schematically illustrating another aspect of the present invention.

FIG. 5 illustrates an optional water and salt recovery in the desalination treatment 12 operating under batch flow or continuous flow conditions. As the high salt bioglycerin 14 may be received, it can be subjected to a desalination treatment 12 to provide a desalinated bioglycerin 20. In the desalination treatment 12, both recovered water 114 and recovered inorganic salt 116 may be salvaged and used to either provide additional products and/or prevent additional waste streams. Besides the desalinated bioglycerin 20 and/or a purified bioglycerin 40 for and the production of biobased chemicals 50, the recovered water 114 and recovered inorganic salt 116 can be considered as additional products from the desalination treatment 12 rather than unwanted by-products or waste streams.

FIG. 6 shows an optional exchange resin regeneration 118 in the desalination treatment 12 operating under batch flow or continuous flow. After the high salt bioglycerin 14 is received, it may undergo a desalination treatment 12 to provide the desalinated bioglycerin 20. This desalination treatment 12 can use ion exchange resins to desalinate the high salt bioglycerin 14. Ion exchange resins are polymers that are capable of exchanging particular cations or anions within the polymer with ions within a solution that is passed through the ion exchange resins.

One of the advantages of using an ion exchange treatment or process to desalinate the high salt bioglycerin 14 for other applications can be that the process itself can generate little to no waste. Another advantage may be that the ion exchange resins used in the ion exchange treatment or process can be regenerated and recycled. In other words, the ion exchange resins can be used multiple times, providing a greener process with fewer waste products and minimizing costs with purchasing new ion exchange resins.

The exchange resin regeneration 118 is detailed further in FIG. 7 for the continuous flow process.

FIG. 7 offers a depiction of the desalination treatment 12 with both exchange resin regeneration as well as the salt and water recovery while operating in a continuous flow mode. It also provides several optional methods to control wastes and costs associated with the ion exchange treatment or process and allows for an additional products to be formed, the recovered water 114 and the recovered inorganic salt 116.

In FIG. 7, an exchange resin regeneration 118 can be used to further reduce costs and potential wastes associated with the process. One of the advantages of using an ion exchange treatment or process to desalinate the high salt bioglycerin 14 may be that the process itself generates little to no waste. Like the other green aspects of this process, the ion exchange resins used can be regenerated. In fact, the ion exchange resins can be used multiple times, providing a greener process with fewer waste products and minimizing costs with purchasing new ion exchange resins.

Ion exchange resins are polymers that are capable of exchanging particular ions within the polymer with ions within a solution that is passed through the ion exchange resins. This can occur for anion resin exchangers in the flow anion exchange treatment 86 and for cation exchange resins in the flow cation exchange treatment 96 of FIGS. 4 and 7. The ion exchange resins can be regenerated or loaded with desirable ions by washing the resin with an excess of the desired ions. The ion exchange resin can then be then flushed free of the newly-exchanged ions from desalination of the high salt bioglycerin 14 by contacting the resin with a solution of the desirable ions. Ion exchange resin regeneration may be initiated after most of the active sites on the resin have been exchanged with ions from the high salt bioglycerin 14 and the ion exchange treatment or process may no longer be effective. With exchange resin regeneration 118, the same resin beads can be used over and over again for the flow anion exchange treatment 86 or the flow cation exchange treatment 96, and the ions that need to be removed from the system can be concentrated from the aqueous inorganic salt 112 to give a recovered water 114 and recovered inorganic salt 116.

There are two types of ion exchange resins used in the continuous flow process. The first may be an anion exchange resin and the second may be a cation exchange resin. Whether the anion exchange resin or the cation exchange resin may be used, the regeneration process can be similar. Although the anion exchange resin and the cation exchange resin may be processed similarly, each ion exchange resin can be separately regenerated.

After acting to desalinate the high salt bioglycerin 14 of FIG. 4, either the flow anion exchange treatment 86 or the flow cation exchange treatment 96 can be brought into the regeneration process of FIG. 7. This flow anion exchange treatment 86 or the flow cation exchange treatment 96 may consist of either the anion exchange resin or the cation exchange resin at least partially saturated with ionic impurities removed from the high salt bioglycerin 14. The anion exchange resin can then be put through a saturated anion exchange resin column 102, and the cation exchange resin may then subjected to a saturated cation exchange resin column 108. In these resin columns, the regeneration can occur. These columns can be the same or different columns from that used in the flow anion exchange treatment 86 and flow cation exchange treatment 96.

For the anion exchange resin regeneration, typically an aqueous alkali 100 may be added to the anion exchange resin in the saturated anion exchange resin column 102. In this process, the regenerated anion exchange resin column 104 will be formed along with an aqueous inorganic salt 112. Typically, this aqueous alkali 100 can be sodium hydroxide, potassium hydroxide, aqueous ammonia, or another source of hydroxide anion that may be compatible with the anion exchange resin. From the regenerated anion exchange resin column 104, the anion exchange resin can be reused after it is directed back to the flow anion exchange treatment 86.

Alternatively in the cation exchange resin regeneration, an aqueous mineral acid 106 can be added to the cation exchange resin in the saturated cation exchange resin column 108, and a regenerated cation exchange resin column 110 may be formed along with an aqueous inorganic salt 112. Typically, this aqueous mineral acid 106 can be aqueous hydrochloric acid or sulfuric acid, with sulfuric acid being the less expensive option and could be used to keep costs down. Depending on compatibility with the cation exchange resin, certain other protic acids may be used in the regenerated cation exchange resin column 110. After this regeneration process in the regenerated cation exchange resin column 108, the cation exchange resin can be reused after it is directed back to the flow cation exchange treatment 96.

Besides the regeneration of both the anion and cation exchange resins, the process can also provide recovered water 114 and recovered inorganic salt 116. After both the flow anion exchange treatment 86 and the flow cation exchange treatment 96, an aqueous inorganic salt 112 may be formed. Instead of initiating another waste stream, this aqueous inorganic salt 112 salt can generate yet another profitable chemical source and/or prevent disposal of another waste stream. A separation of the recovered water 114 and recovered inorganic salt 116 can be achieved through evaporation or distillation of the water, or by crystallization of the salt from a saturated solution. The recovered salt may be sold for industrial applications such as road salt, chilling salts, or the like. In some cases, the salt formed during this phase may also be recovered for use as fertilizer or as a material for lowering the freezing point. Other potential applications may also include water softening, food additives, de-icing, and the production of pharmaceuticals and other chemicals.

After the water is removed from the aqueous inorganic salt 112 as recovered water 114, it can either be safely added to the wastewater system or it could be reused elsewhere in the process of FIG. 1 so as to minimize a waste stream.

Figure 8:
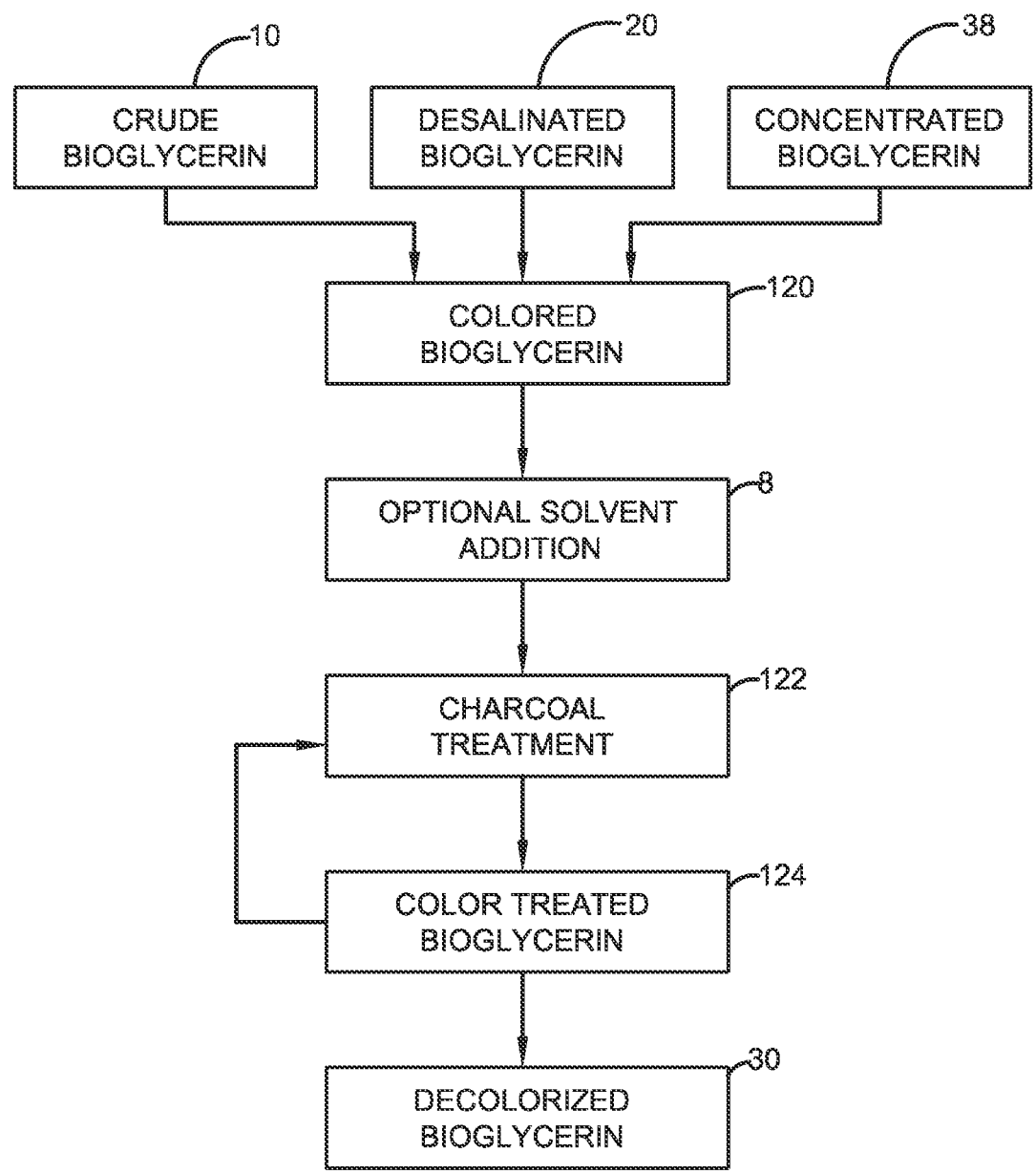
FIG. 8 is a flow diagram schematically illustrating another aspect of the present invention.

FIG. 8 describes a decolorization treatment 22 that can be used in either the batch process or continuous flow process. The decolorization treatment 22 may be done on the crude bioglycerin 10, a desalinated bioglycerin 20, and/or a concentrated bioglycerin 38. At least one of the crude bioglycerin 10, desalinated bioglycerin 20, and/or concentrated bioglycerin 38 can be brought into the treatment as the colored bioglycerin 120.

After the colored bioglycerin 120 is collected, it may undergo an optional solvent addition 8. Like the optional solvent addition 8 in the desalination treatment 12 shown in FIGS. 3 and 4, the decolorization treatment 22 does not require this step. This optional solvent addition 8 can be water or an alcohol like methanol or ethanol or a water/alcohol mixture. This optional solvent addition 8 serves to reduce the viscosity of the colored bioglycerin 120 and helps enhance recovery of the decolorized bioglycerin 30 from the charcoal treatment 122. Optional solvent addition 8 may be recovered in the concentration treatment 32, as shown in FIG. 1.

With or without the optional solvent addition 8, the colored bioglycerin 120 may then be subjected to a charcoal treatment 122. If it is used, the charcoal treatment 122 serves to reduce or remove color and improve the clarity of the resulting decolorized bioglycerin 30. The charcoal treatment 122 may work primarily by an adsorption mechanism. Adsorption is the adhesion of solid materials or dissolved materials onto a surface based on surface energy. During the charcoal treatment 122, the residual fatty acids and colored impurities present in colored bioglycerin 120 can be reduced or removed by adhesion onto an adsorbent charcoal. That is, the charcoal treatment 122 may be a more selective adsorption method for removal of these impurities than it can be for decolorized bioglycerin 30. The colored impurities may adhere to the charcoal treatment 122. This charcoal treatment 122 may provide a lighter colored to a nearly clear decolorized bioglycerin 30. Depending upon the stage of the purification process of FIG. 1, the decolorized bioglycerin 30 can be over 99% pure after removal of an optionally added solvent.

Furthermore, a reduction in the level of residual fatty acid and colored impurities in the colored bioglycerin 120 can be additionally controlled depending on the number 26 of charcoal treatment(s) 122 or processes. Depending on the intended use of the decolorized bioglycerin 30, the optional charcoal treatment 122 may have a variety of different processing methods. These methods may include the additional step of repeating charcoal treatments 122 of the color treated bioglycerin 124. The optional charcoal treatment 122 and the number of its repeating cycles can depend on the color of the colored bioglycerin 120 and level of the colored organic impurities. However, a more decolorized bioglycerin 30 may require increased energy and costs associated with additional cycles of charcoal treatments 122.

After the desired color of the color treated bioglycerin 124 may be achieved through the charcoal treatment(s) 122, the color treated bioglycerin 124 can move to a decolorized bioglycerin 30. The resulting decolorized bioglycerin 30 may be sent to a desalination treatment 12, or concentration treatment 32, or can become a purified bioglycerin 40 for the production of biobased chemicals 50 as illustrated in FIG. 1.

Figure 9:
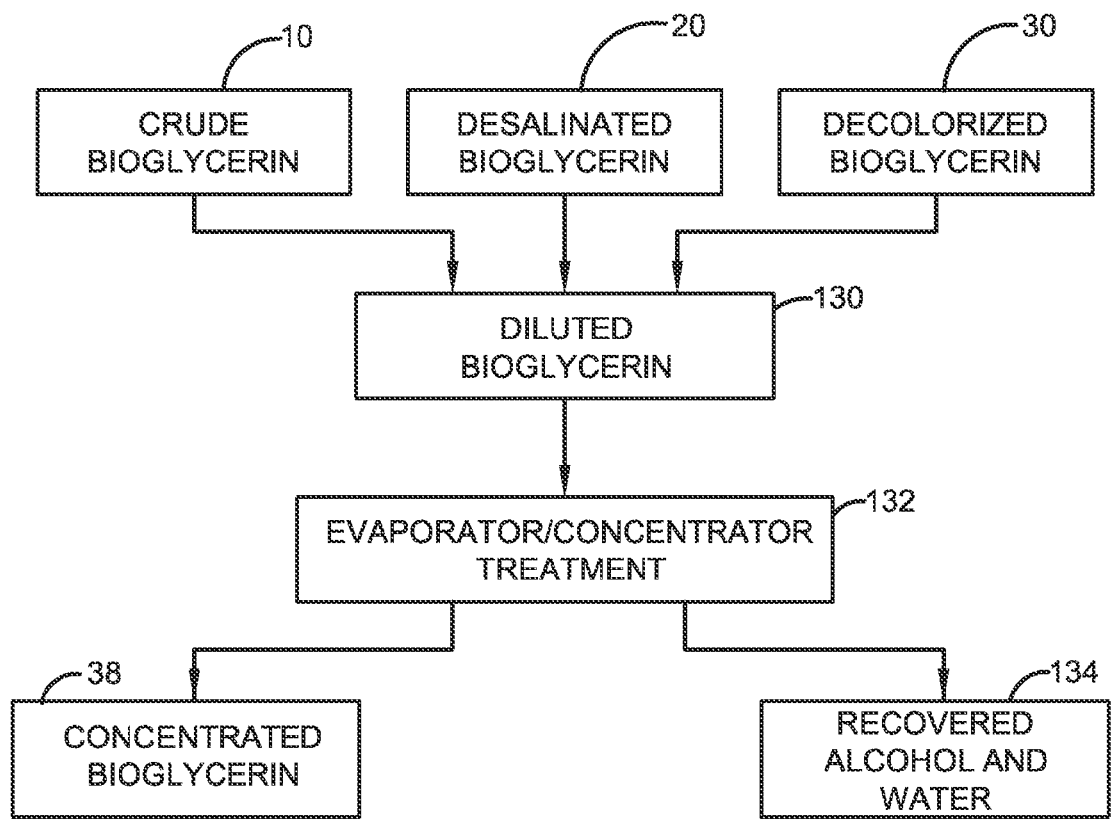
FIG. 9 is a flow diagram schematically illustrating another aspect of the present invention.

FIG. 9 describes the concentration treatment 32 that can be used in either the batch process or continuous flow process. FIG. 9 shows the process in which a diluted bioglycerin 130 may be treated to provide the concentrated bioglycerin 38 and/or recovered alcohol and water 134.

The concentration treatment 32 may be done on the crude bioglycerin 10, a desalinated bioglycerin 20, and/or a decolorized bioglycerin 30. At least one of the crude bioglycerin 10, desalinated bioglycerin 20, and/or decolorized bioglycerin 30 can be brought into the treatment as the diluted bioglycerin 130.

With the concentration treatment 32, the diluted bioglycerin 130 may undergo an evaporator/concentrator treatment 132 to produce the concentrated bioglycerin 38 and/or recovered alcohol and water 134. In the evaporator/concentrator treatment 132, the lower boiling alcohol and water impurities can be separated from diluted bioglycerin 130 under reduced pressure and modest temperatures. These temperatures may be about 25° C. to about 60° C. These reduced pressures may be about 20 mm Hg to about 70 mm Hg. These temperatures may also be higher or the pressures further reduced depending upon the material and equipment capabilities and requirements. By using this concentration treatment 32, both the recovered alcohol and the water 134 may be removed from the diluted bioglycerin 130 and the resulting concentrated bioglycerin 38 may be further processed by a desalination treatment 12, or a decolorization treatment 22, or be sent to a purified bioglycerin 40 for the production of biobased chemicals 50 as shown in FIG. 1.

Figure 10:
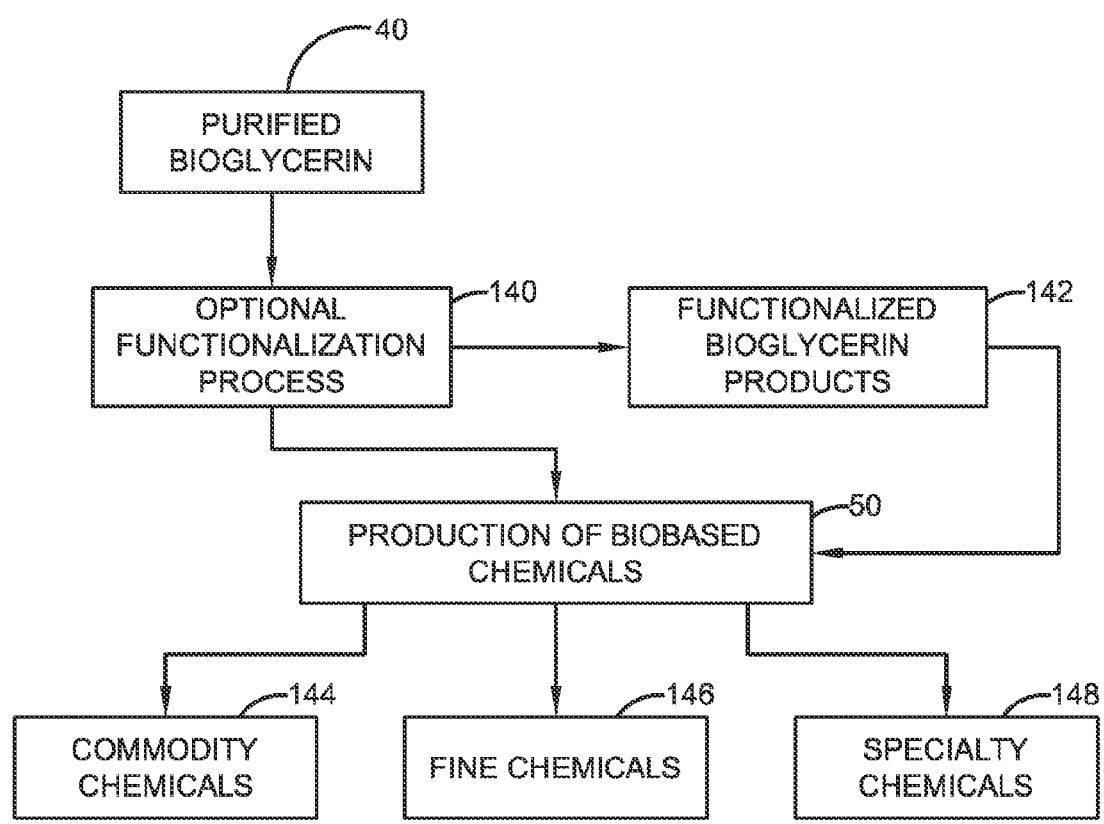
FIG. 10 is a flow diagram schematically illustrating another aspect of the present invention.

FIG. 10 shows a flowchart of several potential derivative products that may be formed from the process. First, the production of biobased chemicals 50 may be provided by a purified bioglycerin 40 of various purities. Alternatively, the production of biobased chemicals 50 may be provided by a crude bioglycerin 10 as shown in FIG. 1. Additionally, an optional functionalization process 140 can also be done to provide both functionalized bioglycerin products 142 and also lead further to the production of biobased chemicals 50. This optional functionalization process 140 may serve to further present added commodity chemicals 144, fine chemicals 146, and/or specialty chemicals 148 that may not be made without this functionalization. This optional functionalization process 140 may include chemical, catalytic and/or biological means of functionalizing the purified bioglycerin 40, and/or the crude bioglycerin 10, prior to the production of biobased chemicals 50. Examples of an optional functional process include, but are not limited to, the preparation of 5- and 6-membered ring acetals and ketals, and selective esterifications and oxidations of one or more of the primary or secondary alcohol centers in the purified bioglycerin 40 or crude bioglycerin 10 to provide functionalized bioglycerin products 142 like solketal and glyceraldehyde.

From the production of biobased chemicals 50, either with or without the optional functionalization process 140, commodity chemicals 144, fine chemicals 146, and/or specialty chemicals 148 may be produced. Several of these commodity chemicals 144, fine chemicals 146, and specialty chemicals 148 may be those shown in FIGS. 11 and 12.

Figure 11:
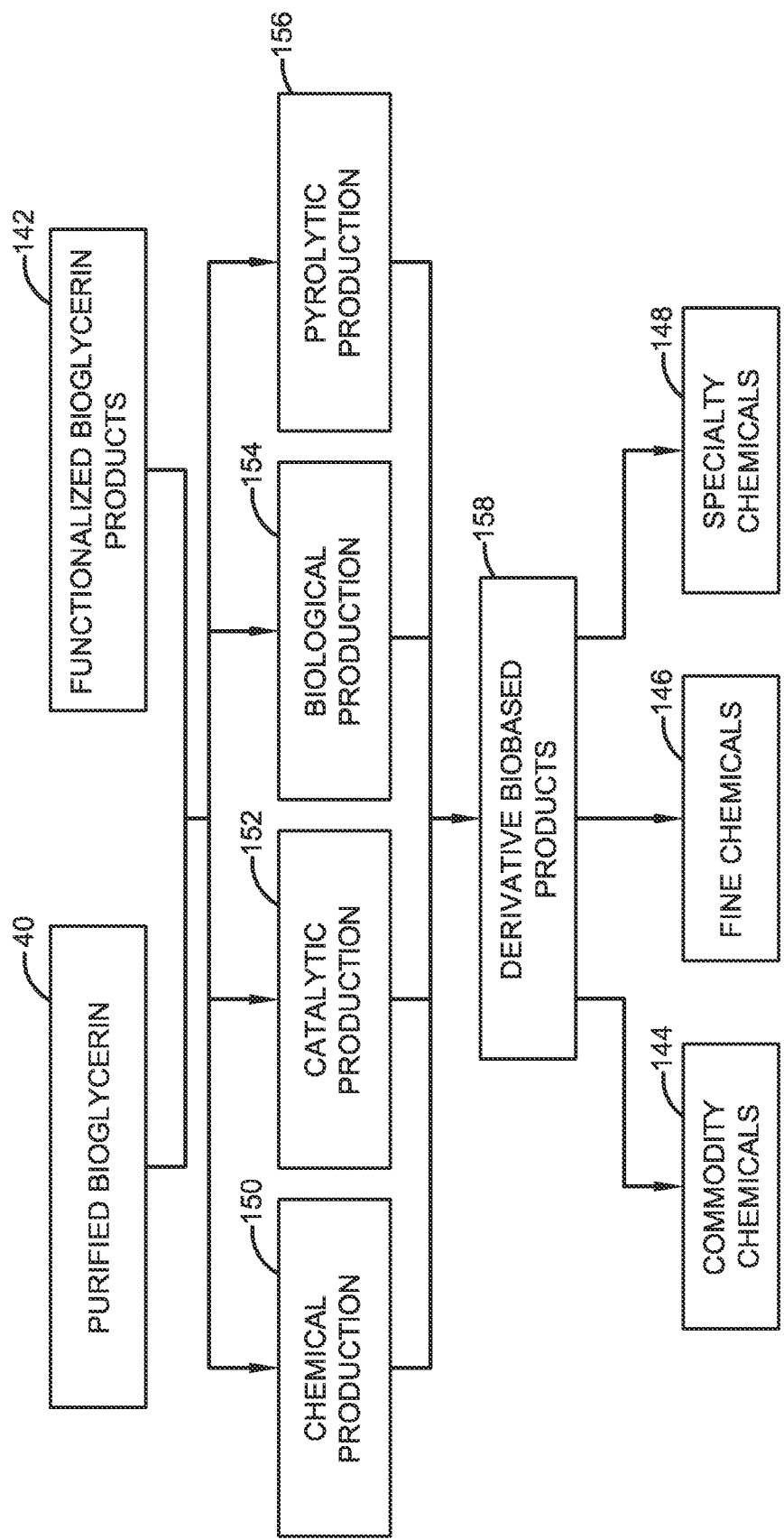
FIG. 11 is a flow diagram schematically illustrating another aspect of the present invention.

FIG. 11 illustrates the production of biobased chemicals 50 from either the purified bioglycerin 40 and/or functionalized bioglycerin products 142. In other instances, the production of biobased chemicals 50 may directly proceed from a crude glycerin 10 as shown in FIG. 1. These derivative biobased products 158 can be converted into commodity chemicals 144, fine chemicals 146, and/or specialty chemicals 148. From FIG. 11, the purified bioglycerin 40 and/or functionalized bioglycerin products 142 may be converted into derivative biobased products 158 through methods of chemical production 150, catalytic production 152, biological production 154, and/or pyrolytic production 156. By using at least one of the conversion 28 methods, including chemical production 150, catalytic production 152, biological production 154, and/or pyrolytic production 156, the purified bioglycerin 40 and/or functionalized bioglycerin products 142 may be able to produce the derivative biobased products 158 that have both financial value by conversion to value-added products and utilization of a low-value by-product/waste stream of biodiesel production 60. Additionally, the plurality of the production of biobased chemicals 50 and/or the derivative biobased products 158 produced from the functionalized bioglycerin products 142 and/or the purified bioglycerin 40 may comprise at least one of achiral, racemic, and optically pure products. These derivative biobased products 158, including commodity chemicals 144, fine chemicals 146, and/or specialty chemicals 148, may be specifically modified to provide at least one of achiral, racemic, and optically pure products. Based on the method of conversion of the purified bioglycerin 40 and/or the functionalized bioglycerin products 142 to the production of biobased chemicals 50, the derivative biobased products 158 may be selectively produced.

Figure 12:
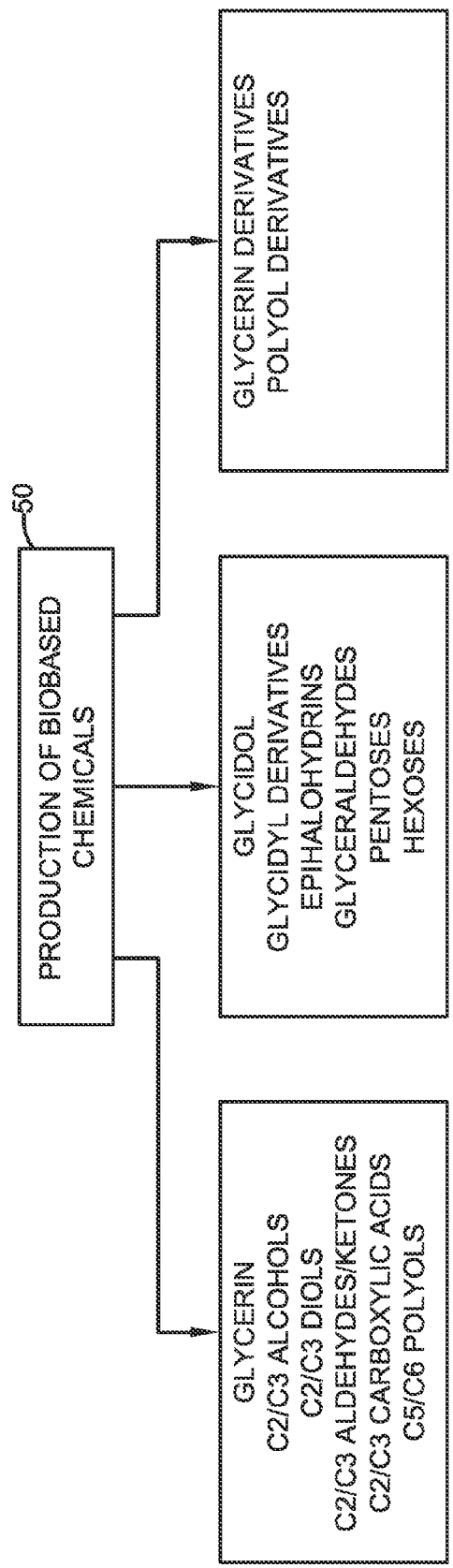
FIG. 12 is a flow diagram schematically illustrating another aspect of the present invention.

FIG. 12 provides some potential end products from the production of biobased chemicals 50. The product categories may include, but are not limited to, purified glycerin and glycerin derivatives, C2/C3 alcohols, C2/C3 diols, C2/C3 aldehydes/ketones, C2/C3 carboxylic acids, C5/C6 polyols and polyol derivatives, glycidol and glycidyl derivatives, glyceraldehyde and glycerin derivatives, and epihalohydrins. Thereunder the production of biobased chemicals 50, a plurality of specific chemicals can be made comprising, but not limited to, ethanol; ethylene glycol; acetaldehyde; glyoxal; acetic acid; glycolic acid; glyoxylic acid; oxalic acid; n-propanol; isopropanol; 1,2-propanediol; 1,3-propanediol; acetone; 1-hydroxyacetone; 1,3-dihydroxyacetone; propionic acid; lactic acid; pyruvic acid; malonic acid; hydroxymalonic acid; high purity glycerin; functionalized glycerins like 4-(hydroxymethyl)-1,3-dioxolan-2-one, 4-methyl-1,3-dioxolane, (2,2-dimethyl-1,3-dioxolan-4-yl)methanol and 1,4-dioxaspiro[4.5]decane-2-methanol; glyceraldehyde; or functionalized glyceraldehydes like 2,2-dimethyl-1,3-dioxolane-4-carbaldehyde and 1,4-dioxaspiro[4.5]decane-2-carbaldehyde; or glycidol; glycidyl ethers like glycidyl methyl ether, glycidyl isopropyl ether, glycidyl n-butyl ether, glycidyl tert-butyl ether, glycidyl allyl ether, glycidyl propargyl ether, glycidyl hexadecyl ether, glycidyl octyl/decyl ether, glycidyl phenyl ether and glycidyl benzyl ether; glycidyl esters like 2-oxiranylmethyl formate, glycidyl butyrate, glycidyl acrylate, glycidyl methacrylate, diglycidyl 1,2-cyclohexanedicarboxylate, glycidyl benzoate and glycidyl 4-nitrobenzoate; epichlorohydrin; epibromohydrin; and polyols like ribitol, arabitol, xylitol, mannitol, sorbitol, galactitol, allitol, and iditol. This production of biobased chemicals 50 as described herein can allow for both the utilization of a renewable, carbonaceous by-product in the production of value-added chemicals and biobased products and an even greener biodiesel production 60 process.

We claim:
1. A method of biorefining, comprising the steps of:
providing bioglycerin;
treating said bioglycerin to provide treated bioglycerin; and
producing at least one derivative product from at least one bioglycerin of said purified bioglycerin and said treated bioglycerin.
2. The method of claim 1, further comprising the step of:
providing bioglycerin as a by-product of biodiesel production.
3. The method of claim 1, wherein the step of treating said bioglycerin to provide treated bioglycerin comprises at least one treatment of desalination treatment, decolorization treatment, and concentration treatment.
4. The method of claim 3, wherein said desalination treatment provides desalinated bioglycerin as said treated bioglycerin.
5. The method of claim 3, wherein said decolorization treatment provides decolorized bioglycerin as said treated bioglcyerin.
6. The method of claim 3, wherein said concentration treatment provides concentrated bioglycerin as said treated bioglycerin.
7. The method of claim 3, wherein the step of treating said bioglycerin to provide desalinated bioglycerin, further comprises the step of:
utilizing a desalination treatment.
8. The method of claim 7, wherein the step of treating said bioglycerin to provide said desalinated bioglycerin, further comprises the step of:
utilizing an ion exchange treatment.
9. The method of claim 8, further comprising the step of:
performing said ion exchange treatment in at least one condition of a batch flow condition and a continuous flow condition.

10. The method of claim 8, further comprising the steps of:
recovering water during said ion exchange treatment; and
recycling said water during said ion exchange treatment.

11. The method of claim 7, further comprising the steps of:
recovering a solvent during said ion exchange treatment; and
recycling said solvent during said ion exchange treatment.

12. The method of claim 8, further comprising the steps of:
regenerating an ion exchange resin during said ion exchange treatment; and
recycling said ion exchange resin during said ion exchange treatment.

13. The method of claim 7, further comprising the step of recovering salt.

14. The method of claim 13, further comprising the step of:
lowering a freezing point of an aqueous solution with said salt.

15. The method of claim 3, wherein the step of treating said bioglycerin to provide decolorized bioglycerin, further comprises the step of:
utilizing a decolorization treatment.

16. The method of claim 5, further comprising the step of:
utilizing activated charcoal in said decolorization treatment.

17. The method of claim 5, further comprising the steps of:
recovering a solvent during said decolorization treatment; and
recycling said solvent during said decolorization treatment.

18. The method of claim 16, further comprising the step of:
performing said decolorization treatment under at least one condition of a batch condition and a continuous flow condition.

19. The method of claim 16, further comprising the steps of:
recovering a solvent during said decolorization treatment with said activated charcoal; and
recycling said solvent during said decolorization treatment with said activated charcoal.

20. The method of claim 3, wherein the step of treating said bioglycerin to provide concentrated bioglycerin, further comprises the step of:
utilizing a concentration treatment.

21. The method of claim 20, further comprising the step of:
utilizing an evaporation or distillation process during said concentration treatment.

22. The method of claim 21, further comprising the steps of:
recovering water during said concentration treatment; and
recycling said water during said concentration treatment.

23. The method of claim 21, further comprising the steps of:
recovering an alcohol during said concentration treatment; and
recycling said alcohol during said concentration treatment.

24. The method of claim 21, further comprising the step of:
performing said concentration treatment under at least one condition of a batch condition and a continuous flow condition.

25. The method of claim 1, wherein said bioglycerin has a weight, said treated bioglycerin has a weight, and said weight of treated bioglycerin is greater than about 80% of said weight of bioglycerin.

26. The method of claim 1, wherein said bioglycerin has a weight, said treated bioglycerin has a weight, and said weight of treated bioglycerin is greater than about 90% of said weight of bioglycerin.

27. The method of claim 1, further comprising the step of selectively producing at least two of said derivative products from at least one bioglycerin of said purified bioglycerin and said treated bioglycerin.

28. The method of claim 1, wherein said producing at least one of said derivative product comprises commodity chemicals, fine chemicals, and specialty chemicals.

29. The method of claim 1, wherein said producing at least one of said derivative product comprises at least one chemical process, biological process, catalytic process, and pyrolytic process.

30. The method of claim 1, further comprising the step of functionalizing said treated bioglycerin prior to production of at least one of said bioglycerin of said purified bioglycerin and said treated bioglycerin of said derivative product.

31. The method of claim 1, wherein at least one of said plurality of derivative products comprises purified glycerin and glycerin derivatives, C2/C3 alcohols, C2/C3 diols, C2/C3 aldehydes/ketones, C2/C3 carboxylic acids, C5/C6 polyols and polyol derivatives, glycidol and glycidyl derivatives, glyceraldehyde and glycerin derivatives, and epihalohydrins produced from at least one of said bioglycerin of said purified bioglycerin and said treated bioglycerin.

32. The method of claim 31, wherein at least one of said C2/C3 alcohols comprises ethanol; n-propanol; and isopropanol.

33. The method of claim 31, wherein at least one of said C2/C3 diols comprises ethylene glycol; 1,2-propanediol; and 1,3-propanediol.

34. The method of claim 31, wherein at least one of said C2/C3 aldehydes/ketones comprises acetaldehyde; glyoxal; acetone; 1-hydroxyacetone; and 1,3-dihydroxyacetone.

35. The method of claim 31, wherein at least one of said C2/C3 carboxylic acids comprises acetic acid; glycolic acid; glyoxylic acid; oxalic acid; propionic acid; lactic acid; pyruvic acid; malonic acid; and hydroxymalonic acid.

36. The method of claim 31, wherein at least one of said purified glycerin and glycerin derivatives comprise purified glycerin; 4-(hydroxymethyl)-1,3-dioxolan-2-one; 4-methyl-1,3-dioxolane, (2,2-dimethyl-1,3-dioxolan-4-yl)methanol; 1,4-dioxaspiro[4.5]decane-2-methanol; glyceraldehyde; 2,2-dimethyl-1,3-dioxolane-4-carbaldehyde; and 1,4-dioxaspiro[4.5]decane-2-carbaldehyde.

37. The method of claim 31, wherein at least one of said glyceraldehyde and glyceraldehyde derivatives comprises glyceraldehyde; 2,2-dimethyl-1,3-dioxolane-4-carbaldehyde; and 1,4-dioxaspiro[4.5]decane-2-carbaldehyde.

38. The method of claim 31, wherein at least one of said glycidol and glycidyl derivatives comprises glycidol, glycidyl methyl ether, glycidyl isopropyl ether, glycidyl n-butyl ether, glycidyl tert-butyl ether, glycidyl allyl ether, glycidyl propargyl ether, glycidyl hexadecyl ether, glycidyl octyl/decyl ether, glycidyl phenyl ether, glycidyl benzyl ether, 2 oxiranylmethyl formate, glycidyl butyrate, glycidyl acrylate, glycidyl methacrylate, diglycidyl 1,2-cyclohexanedicarboxylate, glycidyl benzoate, and glycidyl 4-nitrobenzoate.

39. The method of claim 31, wherein at least one of said glycidyl esters comprises 2-oxiranylmethyl formate, glycidyl butyrate, glycidyl acrylate, glycidyl methacrylate, diglycidyl 1,2-cyclohexanedicarboxylate, glycidyl benzoate, and glycidyl 4-nitrobenzoate.

40. The method of claim 31, wherein at least one of said epihalohydrins comprises epichlorohydrin, and epibromohydrin.

41. The method of claim 31, wherein at least one of said polyols comprise ribitol, arabitol, xylitol, mannitol, sorbitol, galactitol, allitol, and iditol.

42. The method of claim 1, wherein at least one of said derivative products comprises achiral, racemic, and optically pure products.

43. The method of claim 1, further comprising the step of:
using said at least one of said derivative product in the production of other chemicals, materials, and products.

44. The method of claim 4, wherein said desalinated bioglycerin has a weight, and a waste product of said desalinated bioglycerin is less than 60% of said desalinated bioglycerin weight.

45. The method of claim 5, wherein said decolorized bioglycerin has a weight, and a waste product of said decolorized bioglycerin is less than 60% of said decolorized bioglycerin weight.

46. The method of claim 6, wherein said concentrated bioglycerin has a weight, and a waste product of said concentrated bioglycerin is less than 60% of said concentrated bioglycerin weight.

47. A method for biorefining, comprising the steps of:
providing bioglycerin;
treating said bioglycerin to provide treated bioglycerin; and
using waste product from said treated bioglycerin to produce energy.

48. The method of claim 47, wherein said energy is heat or power.

49. A method of biorefining, comprising the steps of:
providing bioglycerin as a by-product of biodiesel production;
treating said bioglycerin to provide at least one bioglycerin of purified bioglycerin and treated bioglycerin;
treating said bioglycerin to provide treated bioglycerin comprising at least one treatment of desalination treatment, decolorization treatment, and concentration treatment;
treating said bioglycerin to provide desalinated bioglycerin using an ion exchange treatment in at least one condition of a batch flow condition and a continuous flow condition;
treating said bioglycerin to provide decolorized bioglycerin using activated charcoal in at least one condition of a batch flow condition and a continuous flow condition;
treating said bioglycerin to provide concentrated bioglycerin using an evaporation or distillation process in at least one condition of a batch flow condition and a continuous flow condition;
treating said bioglycerin with said activated charcoal;
treating said bioglycerin to provide decolorized bioglycerin using activated charcoal in at least one condition of a batch flow condition and continuous flow condition;
treating said bioglycerin to provide concentrated bioglycerin using at least one of an evaporation process and distillation process in at least one condition of a batch flow condition and continuous flow condition;
producing at least one derivative product from said treated bioglycerin by at least one process of a chemical process, biological process, catalytic process, and a pyrolytic process;
recovering and recycling said water, said organic solvent, and said ion exchange resin from said desalination process;
recovering said salt from said desalination process;
recovering and recycling said solvent from said decolorization process;
recovering and recycling said water from said concentration process;
recovering and recycling said alcohol from said concentration process;
recovering said treated bioglycerin, wherein said bioglycerin has a weight, said treated bioglycerin has a weight, and said weight of treated bioglycerin is greater than 80% of said weight of bioglycerin;
reducing a waste product of said treated bioglycerin, wherein said treated bioglycerin has a weight, and said waste product of said treated bioglycerin is less than 60% of said desalinated bioglycerin weight;
producing energy from said waste product of said treated bioglycerin;
functionalizing said bioglycerin and said treated bioglycerin prior to production of at least one of said derivative product; and
producing a plurality of said derivative products comprising purified glycerin and glycerin derivatives, C2/C3 alcohols, C2/C3 diols, C2/C3 aldehydes/ketones, C2/C3 carboxylic acids, C5/C6 polyols and polyol derivatives, glycidol and glycidyl derivatives, glyceraldehyde and glycerin derivatives, and epihalohydrins from said bioglycerin and said treated bioglycerin from said treated bioglycerin.

50. The method of claim 3, wherein the step of treating said bioglycerin to provide desalinated bioglycerin, further comprises the step of:
adding a solvent.

51. The method of claim 3, wherein the step of treating said bioglycerin to provide decolorized bioglycerin, further comprises the step of:
adding a solvent.

* * * * *